United States Patent
Martinez et al.

(10) Patent No.: US 9,594,257 B2
(45) Date of Patent: Mar. 14, 2017

(54) MYOPIA CONTROL MEANS

(71) Applicants: Novartis AG, Basel (CH); Brien Holden Vision Institute, Sydney (AU)

(72) Inventors: Aldo Abraham Martinez, Fort Worth, TX (US); Arthur Ho, Coogee (AU); Padmaja Rajagopal Sankaridurg, Maroubra (AU); Percy Fabian Lazon, Quakers Hill (AU); Brien Anthony Holden, Kingsford (AU); Rick Payor, Cumming, GA (US); Gregor F. Schmid, Canton, GA (US)

(73) Assignees: Novartis AG, Basel (CH); Brien Holden Vision Institute, Sydney (AU)

( * ) Notice: Subject to any disclaimer, the term of this patent is extended or adjusted under 35 U.S.C. 154(b) by 0 days.

(21) Appl. No.: 14/160,393

(22) Filed: Jan. 21, 2014

(65) Prior Publication Data
US 2014/0132933 A1    May 15, 2014

Related U.S. Application Data

(62) Division of application No. 12/988,403, filed as application No. PCT/US2009/041103 on Apr. 20, 2009, now Pat. No. 8,672,473.
(Continued)

(30) Foreign Application Priority Data

Apr. 18, 2008 (AU) .............. 2008901921

(51) Int. Cl.
*G02C 7/02* (2006.01)
*G02C 7/04* (2006.01)
*G02C 7/06* (2006.01)

(52) U.S. Cl.
CPC .............. *G02C 7/041* (2013.01); *G02C 7/02* (2013.01); *G02C 7/04* (2013.01); *G02C 7/06* (2013.01);
(Continued)

(58) Field of Classification Search
CPC . G02C 7/02; G02C 7/04; G02C 7/041; G02C 7/06; G02C 2202/08; G02C 2202/24
(Continued)

(56) References Cited

U.S. PATENT DOCUMENTS 4,155,626 A    5/1979    Grech
4,573,775 A    3/1986    Bayshore
(Continued)

FOREIGN PATENT DOCUMENTS

EP    0745876 A2    12/1996
WO    9712272 A1    4/1997
(Continued)

OTHER PUBLICATIONS

PCT International Search Report dated Sep. 30, 2009, International Application No. PCT/US2009/041103, International Filing Date Apr. 20, 2009.
(Continued)

*Primary Examiner* — Darryl J Collins
(74) *Attorney, Agent, or Firm* — Robert A. Ambrose

(57) ABSTRACT

Sets, kits or stocks of anti-myopia contact or spectacle lenses, along with methods for their use, that do not require a clinician to measure peripheral refractive error in the eyes of myopic patients. Extensive surveys have shown that lenses having peripheral powers or defocus set in accordance with central corrective power will cover almost all normal myopes not worse than −6D central refractive error. In one example, a kit or set of lenses (50, FIG. 15) can have multiple parts or sub-sets (52, 54) each comprising a com-
(Continued)

partmented container (56a, 56b) with lenses (58a, 58b) arranged according to increments of central corrective power (59a, 59b). The lenses (58a) of the first part (52) have four steps (60a, 61a, 62a, 64a) of peripheral power or defocus to provide therapeutic effect and, while the lenses (58b) of the second part (54) also have four steps (60b, 61b, 62b, 64b), the level of therapeutic effect is higher. Other examples of sets, kits and stocks, as well as examples of lenses themselves, are disclosed together with methods of use.

4 Claims, 25 Drawing Sheets

Related U.S. Application Data

(60) Provisional application No. 61/139,060, filed on Dec. 19, 2008.

(52) U.S. Cl.
CPC ..... *G02C 2202/08* (2013.01); *G02C 2202/24* (2013.01)

(58) Field of Classification Search
USPC ............. 351/159.01, 159.02, 159.41, 159.79
See application file for complete search history.

(56) References Cited

U.S. PATENT DOCUMENTS

| | | |
|---|---|---|
| 4,958,924 A | 9/1990 | Parker |
| 5,030,231 A | 7/1991 | Portney |
| 5,121,980 A | 6/1992 | Cohen |
| 5,408,281 A | 4/1995 | Zhang |
| 5,652,638 A | 7/1997 | Roffman |
| 5,691,797 A | 11/1997 | Seidner |
| 5,864,379 A | 1/1999 | Dunn |
| 5,898,473 A | 4/1999 | Seidner |
| 5,929,969 A | 7/1999 | Roffman |
| 6,030,077 A | 2/2000 | Sawano |
| 6,045,578 A | 4/2000 | Collins |
| 6,260,966 B1 | 7/2001 | Sawano |
| 6,286,956 B1 | 9/2001 | Oyama |
| 6,343,861 B1 | 2/2002 | Kris |
| 6,364,481 B1 | 4/2002 | O'Connor |
| 6,364,483 B1 | 4/2002 | Grossinger |
| 6,457,826 B1 | 10/2002 | Lett |
| 6,474,814 B1 | 11/2002 | Griffin |
| 6,540,353 B1 | 4/2003 | Dunn |
| 6,695,449 B2 | 2/2004 | Ye |
| 6,752,499 B2 | 6/2004 | Aller |
| 6,874,887 B2 | 4/2005 | Tyson |
| 7,025,460 B2 | 4/2006 | Smitth |
| 7,036,931 B2 | 5/2006 | Lindacher |
| 7,040,757 B2 | 5/2006 | Hall |
| 7,178,918 B2 | 2/2007 | Griffin |
| 7,287,852 B2 | 10/2007 | Fiala |
| 7,401,922 B2 | 7/2008 | Legerton |
| 7,490,937 B2 | 2/2009 | Ye |
| 7,503,655 B2 | 3/2009 | Smith, III |
| 7,506,983 B2 | 3/2009 | To |
| 7,637,612 B2 | 12/2009 | Menezes |
| 7,665,842 B2 | 2/2010 | Ho |
| 7,766,478 B2 | 8/2010 | Phillips |
| 7,766,482 B2 | 8/2010 | Smith, III |
| 7,803,153 B2 | 9/2010 | Thorn |
| 7,832,859 B2 | 11/2010 | Phillips |
| 7,862,171 B2 | 1/2011 | Varnas |
| 7,909,465 B2 | 3/2011 | Ho |
| 7,992,997 B2 | 8/2011 | Varnas |
| 7,997,725 B2 | 8/2011 | Phillips |
| 7,997,727 B2 | 8/2011 | Ho |
| 8,192,020 B2 | 6/2012 | Goto |
| 8,201,941 B2 | 6/2012 | Choo |
| 8,240,847 B2 | 8/2012 | Holden |
| 2003/0043342 A1 | 3/2003 | Seidner |
| 2003/0058404 A1 | 3/2003 | Thorn |
| 2003/0107703 A1* | 6/2003 | Cox et al. ..................... 351/161 |
| 2003/0123024 A1 | 7/2003 | Dunn |
| 2004/0201821 A1 | 10/2004 | Tyson |
| 2004/0237971 A1 | 12/2004 | Radhakrishnan |
| 2005/0041203 A1 | 2/2005 | Lindacher |
| 2005/0105047 A1 | 5/2005 | Smitth, III |
| 2005/0200809 A1* | 9/2005 | Dreher ............. B29D 11/00413 351/246 |
| 2006/0015180 A1 | 1/2006 | Peyman |
| 2006/0082729 A1 | 4/2006 | To |
| 2006/0176572 A1 | 8/2006 | Fiala |
| 2007/0115431 A1 | 5/2007 | Smith, III |
| 2007/0159601 A1 | 7/2007 | Ho |
| 2007/0258143 A1 | 11/2007 | Portney |
| 2007/0296916 A1 | 12/2007 | Holden |
| 2008/0062380 A1 | 3/2008 | Phillips |
| 2008/0084534 A1 | 4/2008 | Lindacher |
| 2008/0212022 A1 | 9/2008 | Ye |
| 2008/0218687 A1 | 9/2008 | Phillips |
| 2008/0309882 A1 | 12/2008 | Thorn |
| 2009/0161065 A1 | 6/2009 | Smith, III |
| 2009/0257026 A1 | 10/2009 | Varnas |
| 2009/0303442 A1 | 12/2009 | Choo |
| 2009/0310082 A1 | 12/2009 | Varnas |
| 2010/0057202 A1 | 3/2010 | Bogaert |
| 2010/0110371 A1 | 5/2010 | Ho |
| 2010/0225883 A1 | 9/2010 | Ho |
| 2010/0296050 A1 | 11/2010 | Goto |
| 2010/0296058 A1 | 11/2010 | Ho |
| 2011/0001923 A1 | 1/2011 | Phillips |
| 2011/0032474 A1 | 2/2011 | Lindacher |
| 2011/0037944 A1 | 2/2011 | Varnas |

FOREIGN PATENT DOCUMENTS

| | | |
|---|---|---|
| WO | WO 01/08605 A1 | 2/2001 |
| WO | 0153878 A1 | 7/2001 |
| WO | 02088831 A1 | 11/2002 |
| WO | 2005055891 A1 | 6/2005 |
| WO | 2006004440 A2 | 1/2006 |
| WO | 2007041796 A1 | 4/2007 |
| WO | 2007075975 A2 | 7/2007 |
| WO | 2007082268 A2 | 7/2007 |
| WO | 2007092853 A2 | 8/2007 |
| WO | 2007146673 A2 | 12/2007 |
| WO | 2008014544 A1 | 2/2008 |
| WO | 2008031166 A1 | 3/2008 |
| WO | 2008045847 A2 | 4/2008 |
| WO | 2008116270 A1 | 10/2008 |
| WO | 2008131479 A1 | 11/2008 |
| WO | 2009129528 A1 | 10/2009 |

OTHER PUBLICATIONS

PCT Written Opinion of the International Searching Authority dated Sep. 30, 2009, International Application No. PCT/US2009/041103, International Filing Date Apr. 20, 2009.

Authors: David A. Atchison, Catherine E. Jones, Katrina L. Schmid, Nicola Pritchard, James M. Pope, Wendy E. Strugnell, and Robyn A. Riley Name of Article: Eye Shape in Emmetropia and Myopia Published in: Investigative Ophthalmology & Visual Science, Oct. 2004, vol. 45, No. 10, pp. 3380-3386 Copyright: © Association for Research in Vision and Ophthalmology.

Authors: Krish D. Singh, Nicola S. Logan, and Bernard Gilmartin Name of Article: Three-Dimensional Modeling of the Human Eye Based on Magnetic Resonance Imaging Published in: Investigative Ophthalmology & Visual Science, Jun. 2006, vol. 47, No. 6, pp. 2272-2279 Copyright: © Association for Research in Vision and Ophthalmology.

Authors: Donald O. Mutti, Robert I. Sholtz, Nina E. Friedman, and Karla Zadnik Name of Article: Peripheral Refraction and Ocular Shape in Children Published in: Investigative Ophthalmology &

(56) References Cited

OTHER PUBLICATIONS

Visual Science, Apr. 2000, vol. 41, No. 5, pp. 1022-1030 Copyright: © Association for Research in Vision and Ophthalmology.
Authors: David R. Williams, Pablo Artal, Rafael Navarro, Matthew J. McMahon, David H. Brainard Name of Article: Off-axis Optical Quality and Retinal Sampling in the Human Eye Published in: Vision Research, Apr. 1996, vol. 36., No. 8, pp. 1103-1114 Publisher: 1996 Elsevier Science Ltd.

* cited by examiner

Fig. 12

| Central Refractive Error (D) | Median Peripheral Refractive Error (D) | Median Script (Survey) Cent/ Periph. | Add Stepped Peripheral Power / Defocus to Lens | |
|---|---|---|---|---|
| | | | Mild (Add 1.0 to 2.5 D) | High (Add 1.50 to 3.00 D) |
| + 0.25 | − 0.71 | − 0.25 / + 0.96 | − 0.25 / + 1.00 | − 0.25 / + 1.50 |
| + 0.50 | − 0.46 | − 0.50 / + 0.96 | − 0.50 / + 1.00 | − 0.50 / + 1.50 |
| + 0.75 | − 0.21 | − 0.75 / + 0.96 | − 0.75 / + 1.00 | − 0.75 / + 1.50 |
| + 1.00 | − 0.34 | − 1.00 / + 1.34 | − 1.00 / + 1.50 | − 1.00 / + 2.00 |
| + 1.25 | − 0.09 | − 1.25 / + 1.34 | − 1.25 / + 1.50 | − 1.25 / + 2.00 |
| + 1.50 | − 0.02 | − 1.50 / + 1.52 | − 1.50 / + 1.50 | − 1.50 / + 2.00 |
| + 1.75 | + 0.23 | − 1.75 / + 1.52 | − 1.75 / + 1.50 | − 1.75 / + 2.00 |
| + 2.00 | + 0.64 | − 2.00 / + 1.36 | − 2.00 / + 1.50 | − 2.00 / + 2.00 |
| + 2.25 | + 0.89 | − 2.25 / + 1.36 | − 2.25 / + 1.50 | − 2.25 / + 2.00 |
| + 2.50 | + 1.16 | − 2.50 / + 1.34 | − 2.50 / + 1.50 | − 2.50 / + 2.00 |
| + 2.75 | + 1.41 | − 2.75 / + 1.34 | − 2.75 / + 1.50 | − 2.75 / + 2.00 |
| + 3.00 | + 1.19 | − 3.00 / + 1.81 | − 3.00 / + 2.00 | − 3.00 / + 2.50 |
| + 3.25 | + 1.44 | − 3.25 / + 1.81 | − 3.25 / + 2.00 | − 3.25 / + 2.50 |
| + 3.50 | + 1.80 | − 3.50 / + 1.70 | − 3.50 / + 2.00 | − 3.50 / + 2.50 |
| + 3.75 | + 2.05 | − 3.75 / + 1.70 | − 3.75 / + 2.00 | − 3.75 / + 2.50 |
| + 4.00 | + 1.90 | − 4.00 / + 2.10 | − 4.00 / + 2.50 | − 4.00 / + 3.00 |
| + 4.25 | + 2.15 | − 4.25 / + 2.10 | − 4.25 / + 2.50 | − 4.25 / + 3.00 |
| + 4.50 | + 2.84 | − 4.50 / + 1.66 | − 4.50 / + 2.50 | − 4.50 / + 3.00 |
| + 4.75 | + 3.09 | − 4.75 / + 1.66 | − 4.75 / + 2.50 | − 4.75 / + 3.00 |
| + 5.00 | + 2.83 | − 5.00 / + 2.17 | − 5.00 / + 2.50 | − 5.00 / + 3.00 |
| + 5.25 | + 3.08 | − 5.25 / + 2.17 | − 5.25 / + 2.50 | − 5.25 / + 3.00 |
| + 5.50 | + 3.33 | − 5.50 / + 2.17 | − 5.50 / + 2.50 | − 5.50 / + 3.00 |
| + 5.75 | + 3.58 | − 5.75 / + 2.17 | − 5.75 / + 2.50 | − 5.75 / + 3.00 |
| + 6.00 | + 4.31 | − 6.00 / + 1.69 | − 6.00 / + 2.50 | − 6.00 / + 3.00 |

Rotationally Symmetrical Lens Designs

| Central Refractive Error (D) | Median Temporal Refractive Error (D) | Median Nasal Refractive Error (D) | Median Script (Survey) Prescription Cent. / Temporal | Median Script (Survey) Prescription Cent. / Nasal | Add Stepped Peripheral Power Temporal Chosen Power/Defocus | Add Stepped Peripheral Power Nasal Chosen Power/Defocus |
|---|---|---|---|---|---|---|
| + 0.25 | − 0.71 | − 0.43 | − 0.25 / + 0.96 | − 0.25 / + 0.68 | − 0.25 / + 1.50 | − 0.25 / + 1.00 |
| + 0.50 | − 0.46 | − 0.18 | − 0.50 / + 0.96 | − 0.50 / + 0.68 | − 0.50 / + 1.50 | − 0.50 / + 1.00 |
| + 0.75 | − 0.21 | + 0.07 | − 0.75 / + 0.96 | − 0.75 / + 0.68 | − 0.75 / + 1.50 | − 0.75 / + 1.00 |
| + 1.00 | − 0.34 | + 0.19 | − 1.00 / + 1.34 | − 1.00 / + 0.81 | − 1.00 / + 2.00 | − 1.00 / + 1.50 |
| + 1.25 | − 0.09 | + 0.44 | − 1.25 / + 1.34 | − 1.25 / + 0.81 | − 1.25 / + 2.00 | − 1.25 / + 1.50 |
| + 1.50 | − 0.02 | + 0.50 | − 1.50 / + 1.52 | − 1.50 / + 1.00 | − 1.50 / + 2.00 | − 1.50 / + 1.50 |
| + 1.75 | + 0.23 | + 0.75 | − 1.75 / + 1.52 | − 1.75 / + 1.00 | − 1.75 / + 2.00 | − 1.75 / + 1.50 |
| + 2.00 | + 0.64 | + 0.75 | − 2.00 / + 1.36 | − 2.00 / + 1.25 | − 2.00 / + 2.00 | − 2.00 / + 1.50 |
| + 2.25 | + 0.89 | + 1.00 | − 2.25 / + 1.36 | − 2.25 / + 1.25 | − 2.25 / + 2.00 | − 2.25 / + 1.50 |
| + 2.50 | + 1.16 | + 1.68 | − 2.50 / + 1.34 | − 2.50 / + 0.82 | − 2.50 / + 2.00 | − 2.50 / + 1.50 |
| + 2.75 | + 1.41 | + 1.93 | − 2.75 / + 1.34 | − 2.75 / + 0.82 | − 2.75 / + 2.00 | − 2.75 / + 1.50 |
| + 3.00 | + 1.19 | + 1.93 | − 3.00 / + 1.81 | − 3.00 / + 1.07 | − 3.00 / + 2.50 | − 3.00 / + 1.50 |
| + 3.25 | + 1.44 | + 2.18 | − 3.25 / + 1.81 | − 3.25 / + 1.07 | − 3.25 / + 2.50 | − 3.25 / + 1.50 |
| + 3.50 | + 1.80 | + 2.32 | − 3.50 / + 1.70 | − 3.50 / + 1.18 | − 3.50 / + 2.50 | − 3.50 / + 2.00 |
| + 3.75 | + 2.05 | + 2.57 | − 3.75 / + 1.70 | − 3.75 / + 1.18 | − 3.75 / + 2.50 | − 3.75 / + 2.00 |
| + 4.00 | + 1.90 | + 2.64 | − 4.00 / + 2.10 | − 4.00 / + 1.36 | − 4.00 / + 3.00 | − 4.00 / + 2.00 |
| + 4.25 | + 2.15 | + 2.89 | − 4.25 / + 2.10 | − 4.25 / + 1.36 | − 4.25 / + 3.00 | − 4.25 / + 2.00 |
| + 4.50 | + 2.84 | + 3.12 | − 4.50 / + 1.66 | − 4.50 / + 1.38 | − 4.50 / + 3.00 | − 4.50 / + 2.00 |
| + 4.75 | + 3.09 | + 3.37 | − 4.75 / + 1.66 | − 4.75 / + 1.38 | − 4.75 / + 3.00 | − 4.75 / + 2.00 |
| + 5.00 | + 2.83 | + 4.28 | − 5.00 / + 2.17 | − 5.00 / + 0.72 | − 5.00 / + 3.00 | − 5.00 / + 2.00 |
| + 5.25 | + 3.08 | + 4.53 | − 5.25 / + 2.17 | − 5.25 / + 0.72 | − 5.25 / + 3.00 | − 5.25 / + 2.00 |
| + 5.50 | + 3.33 | + 4.78 | − 5.50 / + 2.17 | − 5.50 / + 0.72 | − 5.50 / + 3.00 | − 5.50 / + 2.00 |
| + 5.75 | + 3.58 | + 5.03 | − 5.75 / + 2.17 | − 5.75 / + 0.72 | − 5.75 / + 3.00 | − 5.75 / + 2.00 |
| + 6.00 | + 4.31 | + 5.17 | − 6.00 / + 1.69 | − 6.00 / + 0.83 | − 6.00 / + 3.00 | − 6.00 / + 2.00 |

Rotationally Non-Symmetrical Lenses

Fig. 13

MYOPIA CONTROL MEANS

This application is a divisional application of U.S. Non-Provisional patent application Ser. No. 12/988,403, filed Oct. 18, 2010, which is a national stage filing under 35 U.S.C. 371 of International Application No. PCT/US09/041103 filed Apr. 20, 2009, which claims benefits of Australian Provisional Application No. 2008901921 filed on Apr. 18, 2008 and of U.S. Provisional Application No. 61/139,060 filed Dec. 19, 2008, each of which is incorporated by reference in its entirety.

BACKGROUND OF THE INVENTION

Field of the Invention

The current invention relates to means for inhibiting or ameliorating the progression of myopia, particularly in young people, and includes both methods and apparatus. The methods include procedures for the prescription, selection, fitting and supply of contact and spectacle lenses. The apparatus includes stocks, sets or kits of such lenses and to lenses or lens components per se.

In this specification contact and spectacle lenses capable of—or intended for—both correcting central refractive error and inhibiting the progression (increasing severity) of myopia over time are termed 'anti-myopia' lenses.

Background and Discussion Of Prior Art

Myopia (short-sightedness) is a disorder of the eye in which accommodation of the natural lens can bring near objects but not distant objects to focus on the central retina, distant objects being focused in front of (anterior to) the retina. That is, the focusing power of the eye is too strong 'at distance' for the accommodative power of the eye. The condition is corrected by the use of lenses with negative central refractive power which enable natural accommodation of the lens to focus both near and distant objects on the fovea in the central portion of the retina. Hyperopia (long-sightedness) is a disorder where distant but not near objects can be clearly focused, the condition being corrected by the use of positive power lenses.

Progressive myopia, which is generally considered to be caused by gradually increasing eye length rather than lens power, can be a serious condition that leads to increasing visual impairment despite the use of successively stronger corrective lenses. Some countries in Asia are reporting that more than 80% of youths aged 17 years suffer from myopia and that many are likely to have or develop the progressive condition.

It is generally agreed that normal eye development—called emmetropization—is regulated by a feedback mechanism that controls eye length to allow good central focus by accommodation at both distance and at near—called emmetropia—during animal growth. It is therefore assumed that, in progressive myopia, this feedback mechanism goes awry and causes the eye to continue to lengthen excessively even though good corrective lenses are used. Many conflicting theories have been advanced about the nature of the feedback mechanism and, thus, many different treatments for progressive myopia have been proposed.

It has been proposed, for example, that the feedback mechanism controlling eye growth is somehow upset by deficiencies in the accommodative effort of the eye due to excessive near work. The deficiency is considered to manifest as lag of accommodation (imprecise and insufficient accommodation) at near resulting in defocus, which stimulates further undesirable axial elongation of the eye. Bifocal lenses and PALs (progressive addition lenses) in spectacles were thus employed to relieve the accommodative stress and defocus in the hope that the stimulus for elongation would be removed. However, data from clinical studies showed poor efficacy over the use standard refractive correction using negative power lenses.

U.S. Pat. No. 6,752,499 to Aller teaches prescribing commercially available concentric bifocal contact lenses for myopic eyes that also exhibit near point esophoria to control the progression of myopia. Both distance-center and near-center contact lenses were employed. These lenses, in which both distance and near zones lie within the normal pupil diameter or 'optic zone' of the lens, have the disadvantage that they present two central images to the retina at all times so that image quality is always degraded. In addition, the success of such treatment methods appears to be limited and variable.

In U.S. Pat. No. 6,045,578 to Collins et al. propose that emmetropization is regulated by the degree and direction of spherical aberration present at the fovea. It was proposed that young myopes have higher levels of central negative spherical aberration which promotes inappropriate eye growth and that the use of therapeutic lenses to impart positive central spherical aberration will inhibit excessive axial growth and thus the progression of myopia. We are not aware of the publication of any significant comparative trial using lenses advocated by Collins et al for controlling the progression of myopia. However, we note that the additional spherical aberration further degrades central image quality for both near and distance vision and is, as before, inherently undesirable.

In WO 200604440A2, Phillips et al suggest that simple defocus at the fovea for both distance and near vision inhibits excessive eye growth. They therefore teach the use of a bifocal contact lens that simultaneously provides the central retina with (a) clear vision for both distance and near and (b) myopic defocus for both distance and near. Again, we are not aware of significant published trials reporting the efficacy of this approach and note again that central vision is degraded.

In contrast to the above, U.S. Pat. No. 7,025,460 to Smith et al discloses compelling results of animal trials which demonstrate that it is the nature of the peripheral image, not the central image, that provides the feedback stimulus for emmetropization. (These trials and experiments have been published in prestigious peer-reviewed scientific journals and have received widespread acceptance in the scientific community.) Thus, Smith et al, teach that control of off-axis focus by manipulation of the curvature of field to move the peripheral image progressively in front of the peripheral retina with increasing peripheral angle provides a method of abating, retarding or controlling the progression of myopia. Lenses that manipulate the peripheral image in this way are therefore called 'anti-myopia' lenses as they inhibit myopia progression as well as providing correction of central refractive error. Smith et al noted that hypermetropia or hyperopia (impaired near vision caused by insufficient eye length) could be addressed by manipulation of the curvature of field to move the peripheral image progressively behind the peripheral retina.

International patent application WO/2007/146673 by Holden et al disclosed two-zone anti-myopia lenses that are more easily designed and manufactured than those which manipulate peripheral curvature of field in the manner taught by Smith et al. In such lenses, the central zone that provides the refractive correction needed for good central vision approximates the pupil diameter and is surrounded by a single-focus therapeutic peripheral zone having a refractive power tailored to move at least portion of the peripheral image in front of the retina.

While we have confirmed the work of Smith et al and agree with Holden et al that a two-zone anti-myopia lens is easier to design and manufacture, the implementation of the Smith/Holden teachings in practice is still not straight forward as it requires instruments, training and facilities for the measurement of peripheral refraction that are not widely available, especially in the less affluent countries where progressive myopia is a severe problem. The correct prescription of anti-myopia lenses with a peripheral zone tailored to a patient's eye requires, for example, (i) a peripheral refractometer that is capable of reliably determining peripheral focus, (ii) trained professionals who can use such refractometers with appropriate skill and who can accurately specify the characteristics of corrective lens required for a particular patient, as well as (iii) the presence of a lens manufacturing facility that is capable of making custom lenses with prescribed central and peripheral profiles to order. The associated costs may well put such anti-myopia lenses beyond the reach of those most in need, despite being simpler to design and specify than the 'progressive' anti-myopia lenses of Smith et al.

At this point, three matters of terminology need to be clarified: how the severity of myopia is indicated, the difference between conventional bifocal lenses and anti-myopia lenses, and, the use of absolute and relative terms to indicate the peripheral power of a lens.

First, it is conventional to refer to a patient as, say, a 'minus 3 D myope' meaning that the patient needs or wears −3 Diopter ("D") corrective lenses. This can be confusing because the patient has a +3 D refractive error and could—with some logic—be called 'a +3 D myope'. Since the conventional terminology is entrenched, it will be used herein but care will be taken herein to indicate whether the refractive error of the eye or the power of the corrective lens is intended.

Second, a conventional bifocal lens has two central optic zones of different refractive power, one enabling good central distance vision and the other enabling good central near vision. In bifocal spectacle lenses, the near zone is formed in the lower portion of the lens and the distance zone is formed in the central and/or upper portions of the lens. This allows the desired zone and image to be automatically selected by normal eye movement so a single image is presented to the eye. Because conventional bifocal contact lenses are located on the cornea and move with the eye, both the distance and near zones are located in the central portion of the lens that approximates normal pupil diameter. Thus, both the corrected distance and near images are always presented to the fovea simultaneously and it is left to the brain to direct attention to one or the other, but each image is necessarily degraded by the other. Anti-myopia lenses are not inherently—or even preferably—bifocal in that they are not concerned to provide good near and distance central vision using different central optical zones. Instead, anti-myopia lenses normally have a central refractive zone to correct central myopic refractive error and provide good central vision and a peripheral 'therapeutic' refractive zone outside the central zone to inhibit continued eye growth. However, anti-myopia lenses can be bifocal, in which case they would have two central zones like a conventional bifocal lens in addition to the therapeutic peripheral zone.

Third, the difference between the refractive power of the central and peripheral zones of an anti-myopia lens is often referred to as 'peripheral defocus' because it is conventional to specify lenses in terms of a base corrective refractive power applied to the whole optic zone and to regard a different power in the periphery to be a modification of the base power. Thus, when the peripheral refractive power is less negative than the central power, the corrective lens is said to have peripheral 'myopic defocus' and, when the peripheral refractive power is more negative than the central power, the lens is said to have 'hyperopic defocus' in the periphery. This is confusing if the change in peripheral power improves focus in the periphery. On the other hand, as the peripheral defocus of many anti-myopia lenses is increased to ensure that the peripheral image is in front of the retina, these lenses may cause focal error or blur in the peripheral retina. In this specification, 'peripheral defocus' will be used conventionally for the relative difference between peripheral and central refractive power of an anti-myopia lens and 'peripheral power' will indicate the absolute refractive power in the periphery of the optic zone of a lens. It will be appreciated, however, that peripheral defocus and peripheral power are essentially equivalent since one can readily be derived from the other if the central power of the lens is known. It should also be noted that the peripheral defocus may be different for different radial distances on a lens if the peripheral power and/or central power of the lens is not constant with radius. Finally, the peripheral mis-focus perceived by a patient fitted with an anti-myopia contact or spectacle lens will be called 'blur' or 'peripheral blur'.

BRIEF SUMMARY OF THE INVENTION

While we appreciate the scientific contribution of Smith et al, as published in both the scientific and patent literature, and while we recognize the practical benefit of the two-zone anti-myopia lenses proposed by Holden et al, we are nevertheless concerned about the cost of providing Smith/Holden anti-myopia lenses and therapies to myopes, particularly to young myopes in developing countries where progressive myopia is common and debilitating.

Since our research indicated that the optimal area of the peripheral image to manipulate for a two-zone anti-myopia lens is that affected by an incident peripheral ray at an angle of about 30 degrees, we undertook extensive surveys of the eyes of young myopes in Australia and China in which central and peripheral refractive errors were measured at this angle both with and without their conventional corrective lenses in place. Peripheral error was measured at approximately 30 degrees to the visual axis for the temporal, nasal and superior quadrants of the retina. From other studies, we also considered that—as far as the problem of progressive myopia is concerned—the population of young myopes surveyed is generally representative of −0.25 D to −6 D myopes worldwide. This cohort or group can be termed 'normal myopes' to distinguish them from extreme or pathological myopes that are significantly worse than −6 D. In short, we believe that our strategies for inhibiting progressive myopia, as disclosed herein, can be generally applied to normal myopes. The survey data is summarized in FIGS. 3-11 but more detailed and technical publications will occur in the scientific literature.

In summary, our survey data revealed that:
(i) Surprisingly, and in apparent conflict with the teachings of Smith et al, almost all unaided eyes with significant myopia (greater than +1.75 D central refractive error) were not hyperopic in the periphery. Only those with central refractive errors less than +1.75 D were slightly (less than −1.0 D) hyperopic in the periphery, and this tended to be in the temporal quadrant of the eye.

(ii) The degree of peripheral refractive error at 30 degrees (incident) in the unaided eye is generally positively related to the degree of central refractive error, being more closely proportional in the nasal meridian. For unaided eyes with central refractive errors increasing from about +1.75 D to about +3.75 D this peripheral refractive error increased roughly proportionately from zero to about +2 D and, for central errors increasing from about +4.0 D to about +6.0 D, the peripheral error increased from about +2.0 D to a little over about +4.0 D, again in substantial proportion.

(iii) Thus, instead of the worst unaided myopes being the most hyperopic in the periphery they were the most myopic; that is, they should have had the greatest inhibition of eye growth according to Smith et al.

The apparent conflict between our survey findings and the teachings of Smith et al is readily resolved when overall refractive errors are measured on 'aided eyes'; that is, with the subject's habitual contact or spectacle lenses in place. It is then found that practically all aided myopic eyes are hyperopic in the periphery and that the greater the central refractive correction the greater the peripheral hyperopia. In other words, by making the power of the conventional lens sufficiently negative to bring the central focus onto the retina, the peripheral focus of the aided eye is moved back behind the retina making the periphery hyperopic and generating the stimulus for further eye growth. Ironically, for −4 D to −6 D myopes (ie, at the higher end of normal), any therapeutic benefit of their substantial (unaided) peripheral myopia is swamped by the peripheral hyperopia imposed by corrective lenses of conventional design. In short, the results of our survey strongly support the basic hypothesis of Smith et al.

Our investigations have shown that the great majority of myopes will accept contact lenses that have 3.0 D myopic peripheral defocus at 30 degrees (incident) and that many will tolerate or get used to a peripheral defocus as high as 3.5 D. Combining this information with the broad survey findings outlined above showed that there is a very high statistical probability (around 95%) that contact-lens-wearing −6 D myopes or better can be fitted from a stock of pre-manufactured anti-myopia contact lenses with a lens that both corrects central error and has a pre-set myopic peripheral defocus sufficient to mitigate myopia progression without intolerable peripheral blur.

While the situation with spectacle-wearing myopes is nominally much the same as for contact lens wearers, their tolerance for peripheral blur may be somewhat reduced because of 'swim'; that is, peripheral blur that changes with eye movement. However, the amount of swim can be generally reduced by adjustment of the base curve of the spectacle lenses.

Producing, using and supplying pre-manufactured sets, kits or stocks of anti-myopia lenses with pre-determined corrective and peripheral powers therefore comprise one aspect of this invention. Another aspect is pre-assembled or pre-manufactured sets, kits or stocks in which the lenses are organized or arrayed according to corrective power and/or according to steps or levels of peripheral defocus so that use and understanding of anti-myopia lenses by clinicians and patients is facilitated. For example, understanding can be facilitated by using only a few steps of peripheral power (so that multiple lenses within a band of central powers share the same peripheral power). In addition or alternatively, a kit with multiple anti-myopia lenses having the same central corrective power but differing levels of peripheral power enable a clinician to select a level of peripheral power, defocus or therapeutic effect based on assessed patient propensity for progressive myopia. Another aspect of the invention therefore relates to methods of prescription and/or trial fitting using the anti-myopia lenses of the present invention.

For contact lenses, it is preferable that the central corrective power of the anti-myopia lenses of the set, kit or stock increases in increments of about −0.25 D, giving about 20 increments over −5 D or about 24 increments over—6 D, but other increments may be used. A larger number lenses with smaller increments is possible but generally not cost-effective while fewer lenses with large increments—for example, −0.33 D or even −0.50 D—may save cost but be less than optimal for the patient. It will be appreciated that the set or kit of contact lenses may include multiple copies or batches of each lens to form a stock of identical lenses to allow multiple identical prescriptions or fittings without the need to restock the set. Normally, the contact lenses will be hygienically packed in sachets identifying the central corrective power, peripheral power or defocus and the treatment level (amount of peripheral defocus). Also, it will be appreciated that not every set, kit or stock of contact lenses formed in accordance with this invention needs to have a full complement of lenses from, say, −0.25 D to −6.0 D, as smaller kits may be more appropriate for specialist clinicians who prefer to treat only certain classes of patients.

The stocks, sets or kits for spectacle lenses can be of quite a different character to those indicated above for contact lenses because they may only comprise a few add-on (eg, clip-on or stick-on) lenses applied to the spectacles used by the patient. Such add-on lenses can have plano center zones and offer the choice of just a few levels of peripheral myopic defocus or power to be selected according to desired therapeutic effect and/or patient tolerance to swim. Here, 'plano' means contributing negligible refractive power to the combined lens. Thus add-on lenses with plano central zones maybe transparent lenticular discs in which the central material has negligible optical power, or they may be ring-like in that there is a central hole rather than any central material. The former are preferred because the physical edge of a hole is avoided and the transition between the plano center and the selected peripheral power can be made gradual. Also, if the add-on lens is not rigid (as in a clip-on lens) but is floppy (as in a peel-off and stick-on sheet-like lens), thin stick-on discs can be more easily handled than thin rings. From another aspect, the invention also comprises add-on spectacle lenses of the type indicated for converting standard spectacle lenses into anti-myopia lenses.

Alternatively, sets, kits or stocks of pre-manufactured finished anti-myopia spectacle lenses with increments of central power and with steps and/or levels of peripheral power (as described above for contact lenses) may be provided or used with the advantage of precision, despite the additional cost involved. Further, bearing in mind the problem of swim in some spectacle lenses, the number or range of pre-manufactured spectacle lenses may be less than for contact lenses. The precise matching of the peripheral and central powers enabled by complete kits of finished trial spectacle lenses can be of particular value for large clinics that have turnkey facilities for finishing base lenses in-house. It will also be appreciated that both contact and spectacle lenses envisaged herein may be rotationally symmetric or asymmetric; that is, some may have substantially the same peripheral defocus in all quadrants while others may have different levels of defocus in different quadrants.

The need for a clinician to measure peripheral refraction of an eye, calculate the adjustment required to secure the desired therapeutic effect, specify a custom lens and have it supplied is thus avoided by the availability of such sets of pre-manufactured anti-myopia lenses. While it is preferable for the clinician to have a set of anti-myopia lenses for trial fitting and/or supply to patients, it may suffice for the clinician to simply determine the central refractive error and the fit or style of the lens and to then order an anti-myopia lens with the appropriate central correction and shape from a stock or kit of lenses held by a manufacturer or wholesaler.

From another aspect, the invention comprises a set, kit or stock of pre-manufactured lenses for providing an anti-myopia lens for an eye of a myopic patient, where each lens has a central optical axis and a central optical zone with a corrective refractive power of less than about −6.0 D and each lens has a peripheral optical zone lying outside the central zone that includes incident angles of around 30 degrees and that has myopic defocus of not more than about 3.5 D. The lenses may be rotationally symmetric having the same peripheral defocus in all quadrants or they may be asymmetric in that the peripheral defocus is concentrated in selected quadrants, the nasal and temporal quadrants of the lenses being preferred. The lenses of the set are arranged in an orderly manner so that a clinician, by selecting a lens for central corrective power, is able to provide a lens which inhibits myopia progression without needing to measure peripheral refractive error in the eye and prescribe a lens with customized peripheral power.

From another aspect, the invention comprises an anti-myopia spectacle lens formed from a base lens with a central corrective optical zone of at least normal pupil diameter, and a therapeutic lens with a plano center attached to the base lens. The therapeutic lens has an annular peripheral zone surrounding the plano center of sufficient size to include incident angles of around 30 degrees and has refractive power that is more positive than that of the central corrective zone of the base lens.

From another aspect, the invention comprises a method of supplying or selecting an anti-myopia lens for a myopic eye which includes the steps of: measuring the central refractive error of the myopic eye, assessing the propensity of the patient for progressive myopia by having regard to patient history, selecting from a set, kit or stock of pre-manufactured lenses a first lens having (i) a central corrective refractive power that best matches the measured central refractive error and (ii) a level of peripheral myopic defocus that best matches the assessed propensity for progressive myopia, trying the first lens on the eye to determine whether the peripheral blur is acceptable and, if so, supplying or prescribing the first lens. If the level of myopic defocus is unacceptable, a second trial lens is selected from the set, kit or stock of with the same the same central corrective power but a reduced level of peripheral myopic defocus.

From another aspect, the method may employ a set, kit or stock of lenses having multiple lenses with the same central corrective refractive power but with different levels of myopic peripheral defocus, the method then comprising the steps of: measuring the central refractive error of the myopic eye, taking the patient's history to assess the patient's propensity for progressive myopia, and supplying, prescribing or selecting a lens having (i) a central refractive power to correct the measured refractive error and (ii) the level of myopic peripheral defocus corresponding to assessed propensity for progressive myopia.

From another aspect, the invention can involve a method of providing an anti-myopia spectacle lens having the steps of: measuring the central refractive error of the eye, judging the propensity of the patient for progressive myopia from the patient history, prescribing and fitting a conventional spectacle lens for the eye to correct the error, selecting an auxiliary lens with a plano central zone surrounded by a peripheral zone with a positive peripheral power appropriate to the judged propensity of the patient for progressive myopia, and coaxially attaching the auxiliary lens to the conventional lens so that the combination of the conventional and auxiliary lens generates a peripheral defocus for inhibiting the progression of myopia in the eye.

From another aspect the invention provides an ophthalmic device, for example an ophthalmic lens, such as a contact lens, for reducing the progression of myopia of an eye, the ophthalmic device comprising a predetermined central sphere power which is defined by an amount of myopia of an eye, and includes a predetermined peripheral power profile which effects a relative peripheral refraction of a corrected eye and which peripheral power profile defines a peripheral defocus. The peripheral defocus is a differential between the central sphere power and the peripheral sphere power along the peripheral power profile, wherein the peripheral defocus is a function of the central sphere power.

From another aspect the invention provides a method for reducing the progression of myopia of an eye, the method comprising placing an ophthalmic device, for example a contact lens, on an eye wherein the device comprises a predetermined central sphere power which is defined by an amount of myopia of an eye, the device further including a predetermined peripheral power profile which effects a myopic defocus, and including a peripheral defocus of the peripheral power profile, wherein the peripheral defocus is a differential between the central sphere power and the peripheral power along the peripheral power profile, wherein the peripheral defocus is a function of the central sphere power.

From another aspect the invention provides a ophthalmic device, for example a contact lens, for reducing the progression of myopia of an eye, the device including a predetermined central sphero-cylindrical power which is defined by an amount of myopia of an eye, a predetermined peripheral power profile which effects a relative peripheral refraction of a corrected eye and a peripheral defocus of the peripheral power profile, wherein the peripheral defocus is a differential between the central sphero-cylindrical power and the peripheral sphere power along the peripheral power profile, and wherein the peripheral defocus is a function of the central sphero-cylindrical power.

In embodiments of these aspects, the peripheral defocus may be defined by the average amount of relative peripheral refraction in a population by sphere power. The peripheral defocus may be approximately first order linear as a constant function of the central sphere power, or may be non-linear as a function of the central sphere power, or may increase non-linearly or decrease non-linearly as a function of the central sphere power. The peripheral defocus up to 30 degrees from the central axis may be between about 0.25 D and 4.00 D, and/or the peripheral defocus up to 40 degrees from the central axis may be between about 0.5 D and about 6.00 D. Also, the ophthalmic device may be part of a series of ophthalmic devices comprising an ophthalmic device having an average peripheral defocus, an ophthalmic device having an above average peripheral defocus and an ophthalmic device having a below average peripheral defocus, wherein the average peripheral defocus is determined by a mean from a defined population.

These and other features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIG. 12 is a tabulation based upon the survey results of FIGS. 6-11 relating measured central and median peripheral refractive errors to different sets of anti-myopia lens characteristics.

FIG. 13 is a tabulation also based upon the survey results of FIGS. 6-11 relating measured, central, nasal and temporal refractive errors to additional different sets of anti-myopia lens characteristics.

FIG. 1 is a greatly simplified diagrammatic sectional plan of a normal left human eye 10 having a cornea 12, iris 14, lens 16, retina 18 and visual axis 20, the nasal plane between the eyes (or mid-visual axis) being indicated at 21. Retina 18 is divided into (i) a central portion 22 (solid black) that is used for central vision and includes the fovea, the most sensitive portion of the retina, and (ii) an annular peripheral portion 24 (hatched) which is much larger in area than central portion 22 but is less sensitive. In a normal or emmetropic eye with a straight-ahead gaze (on axis 20) directed at distance, an axial central beam 26 from a distant object will be brought to focus at f on the fovea in the middle of central region 22 of retina 18 providing good visual acuity. At the same time, a peripheral or off-axis beam 28 from a distant object will be brought to focus at point p on peripheral retina 24, it being assumed that the central ray 28a of peripheral beam 28 intersects visual axis 20 at the axial center n of pupil 14 (sometimes referred to as the nodal point of eye 10). When the gaze is directed at a near on-axis object, the lens 16 changes shape and optical power in a process called 'accommodation' to (ideally) also bring beam 26 from the near object to focus at point f. Similarly, beam 28 from a near off-axis object ideally will be brought to focus at point p on peripheral retina 24. In fact, an emmetropic eye will normally exhibit astigmatism for peripheral off-axis objects so that there will be two slightly different foci near p on the peripheral retina for both near and distance images.

Figure 1:
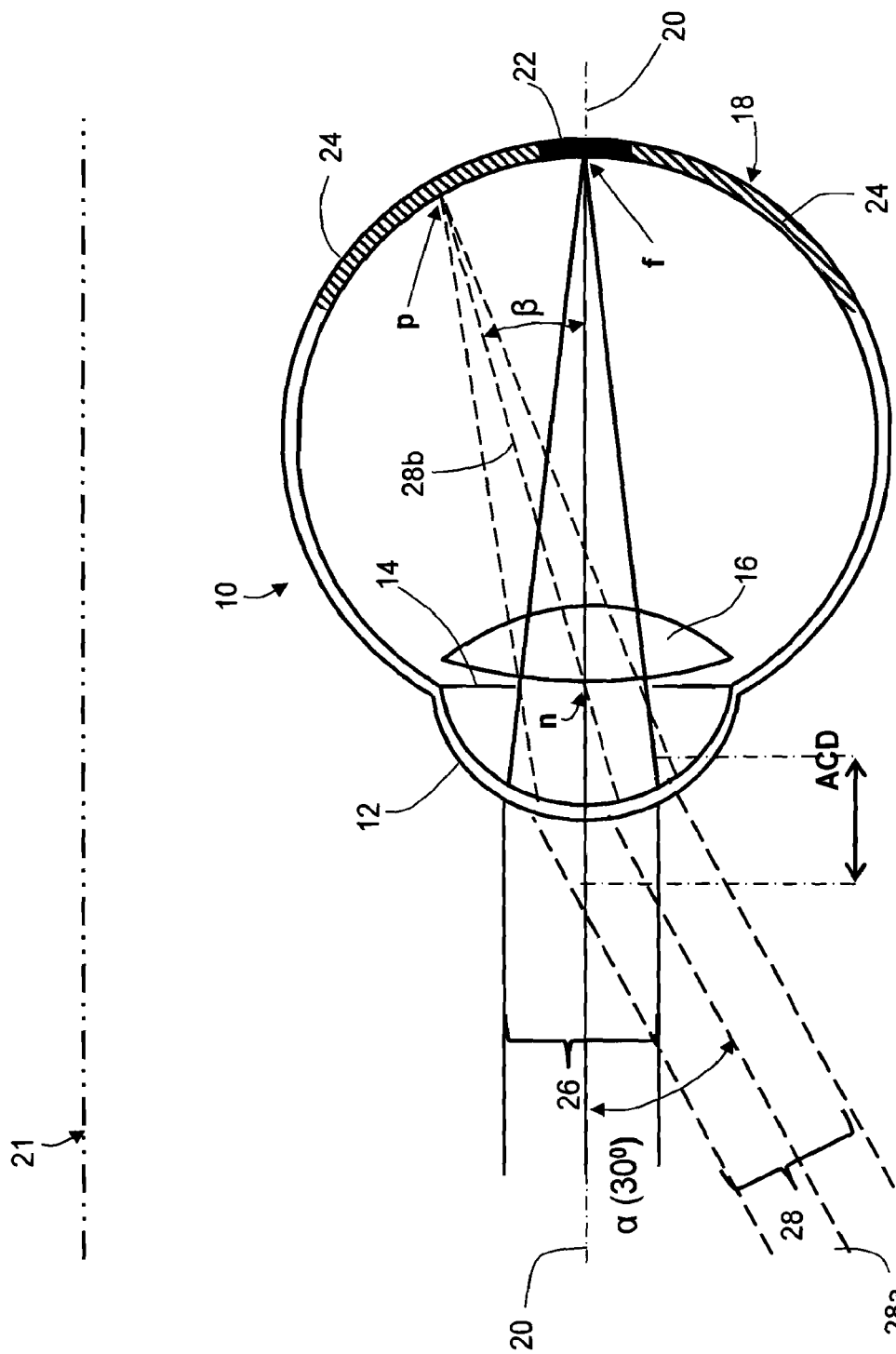
FIG. 1 is a diagrammatic sectional plan of a emmetropic human eye showing various incident light rays to clarify the meaning of terms used in this specification.

It will be noted by inspection of FIG. 1 that peripheral beam 28 enters eye 10 from the temporal side or quadrant of the eye (and head) and is focused on the nasal side or quadrant of peripheral retina 24. Conversely, though not shown, peripheral rays entering eye 10 from the nasal quadrant will impinge on the temporal quadrant of peripheral retina 24. Of course, peripheral rays can enter the eye from the superior quadrant (above) or the inferior quadrant (below).

The work of Smith et al has shown that out-of-focus images on the peripheral retina 24 provide an important stimulus for the regulation of eye growth. Accordingly, the measurement of the refractive power of the eye at off-axis angles is now considered to be of critical importance for correctly prescribing lenses for myopes suffering from progressive myopia. In this specification, the angle α at which central ray 28a of peripheral beam 28 intersects axis 20 at point n is the peripheral angle (or off-axis angle) of that ray or beam. Because of refraction at the cornea 12 and lens 16, the angle β which the emergent central peripheral ray 28b makes with optic axis 20 within eye 10 is less than α and is difficult to determine in vivo with normally available instruments. It is noted that the axial distance between the anterior surface of cornea 12 and the plane of iris 14—often referred to as the anterior chamber depth, or ACD—is generally taken to be 3.5 mm. This distance is identified as ACD in FIGS. 1-3 and is used in measuring the peripheral powers of anti-myopia lenses.

Our research suggests that an incident angle α of 30 degrees in any meridian will place point p far enough into the peripheral retina to provide the desired stimulus for eye growth but is not so oblique as to be excessively difficult to use. Effectively, angle α can be regarded as a solid angle. Accordingly, in our extensive surveys of myopic youth in Australia and China we used an incident peripheral angle α of 30 degrees when measuring the peripheral refraction of aided and unaided eyes. The findings of these surveys have therefore been used to design and test corrective symmetrical and asymmetrical anti-myopia lenses for myopic patients generally.

Figure 2:
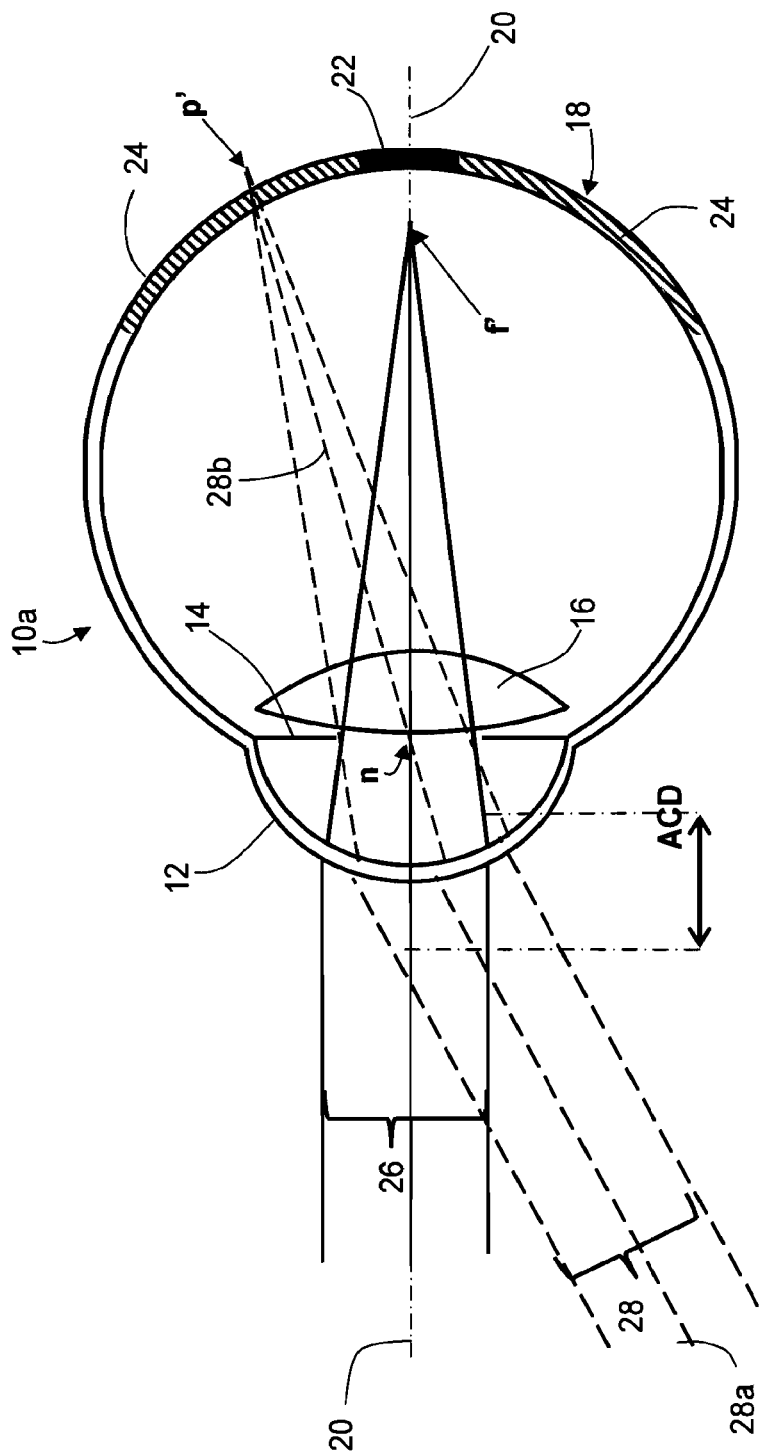
FIG. 2 is a similar diagram to that of FIG. 1 but illustrates—in an exaggerated manner—refractive errors of a typical myopic eye.

FIG. 2 is essentially the same diagram as that of FIG. 1 but shows (very much exaggerated) a myopic eye 10a that is also prone to progressive myopia. (The same reference numerals are used for the same parts as in eye 10 of FIG. 1.) The axial length of eye 10a is too long for accommodation to focus on-axis beam 26 from a distant object onto central retina 22. Instead, it is focused at point f' in front of central retina 22 and distant images will therefore be out-of-focus. For convenience, this problem is commonly regarded as 'refractive error' because can be corrected by fitting a negative power lens (see FIG. 3). However, myopes can typically focus near on-axis objects on central the retina 22 achieve good near vision. Eye 10a illustrates another 'refractive error' common in myopic eyes—peripheral hyperopic defocus—in which off-axis beam 28 is focused behind peripheral retina 24, at p'. Smith et al have shown that hyperopic defocus increases the stimulus for excessive eye growth and contributes to progressive myopia.

Figure 3:
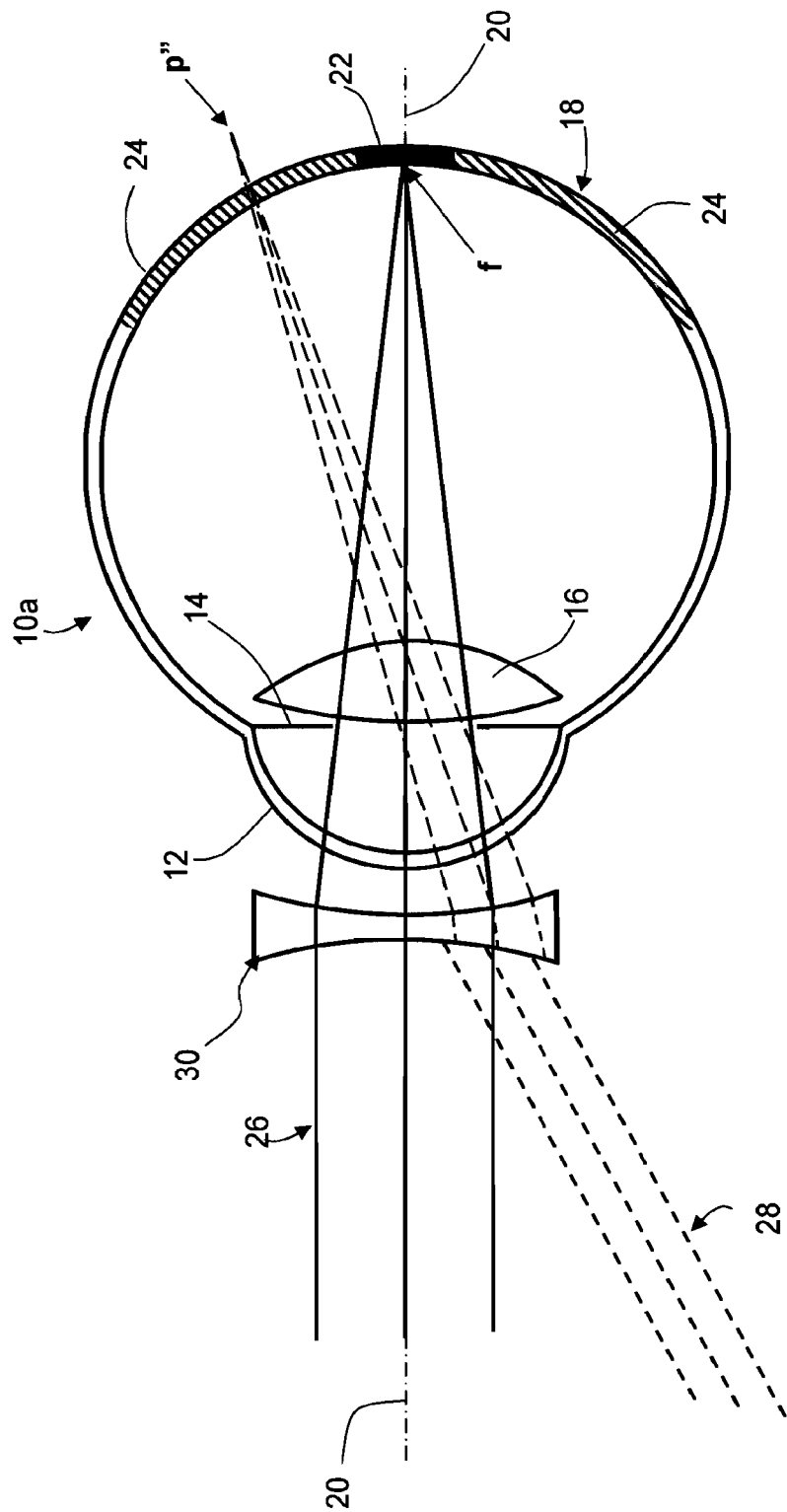
FIG. 3 is a similar diagram to that of FIG. 2 but illustrates the use of a normal lens for correcting central refractive error.
Figure 4:
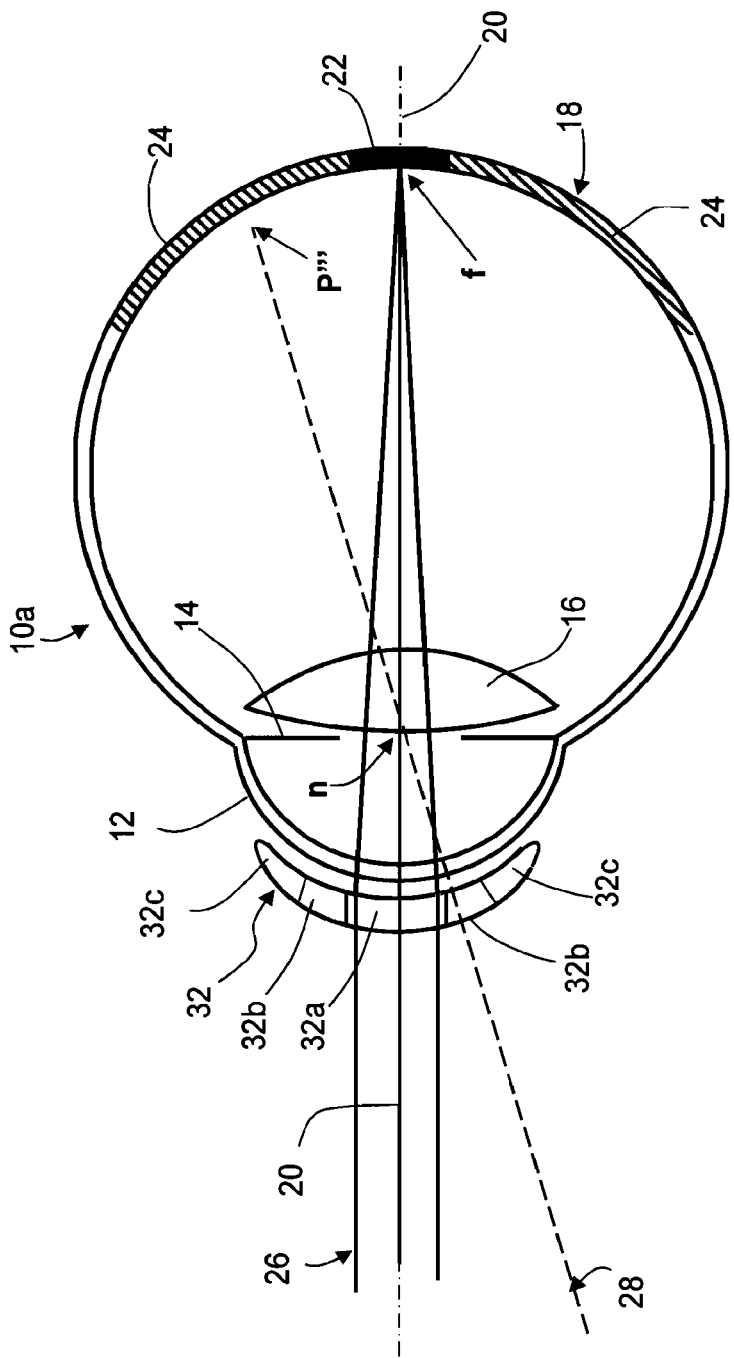
FIG. 4 is a similar diagram to that of FIG. 2 but illustrates the use of an anti-myopia contact lens.

FIG. 3 shows myopic eye 10a fitted with a conventional corrective lens. Though a spectacle lens 30 is illustrated, the same considerations apply to conventional contact lenses. Lens 30 has negative power that nicely corrects central vision to let accommodation of natural lens 16 bring on-axis beam 26 from a distant object to focus on the fovea at f. However, lens 30 shifts the focus of off-axis beam 28 to a point p" further behind peripheral retina 24, generating an even greater stimulus for continued eye growth and progressive myopia. FIG. 4 illustrates the effect of an anti-myopia corrective lens on myopic eye 10a, in this case a contact lens 32. Lens 32 has a central optic zone 32a of about pupil size (normally 4-5 mm diameter for youths under standard room lighting) that corrects central vision to let accommodation of natural lens 16 bring distance central focus onto central retina 22 at point f. Lens 32 has an annular peripheral therapeutic optic zone 32b surrounding central zone 32a with sufficient myopic defocus to bring peripheral beam 28 to focus at point p''' in front of peripheral retina 24, thereby generating a stimulus to inhibit eye growth and progression of myopia in eye 10a. However, the out-of-focus peripheral image can cause peripheral blur. Contact lens 32 has a non-optic zone 32c surrounding peripheral zone 32b to enhance fitting and comfort.

Figure 5:
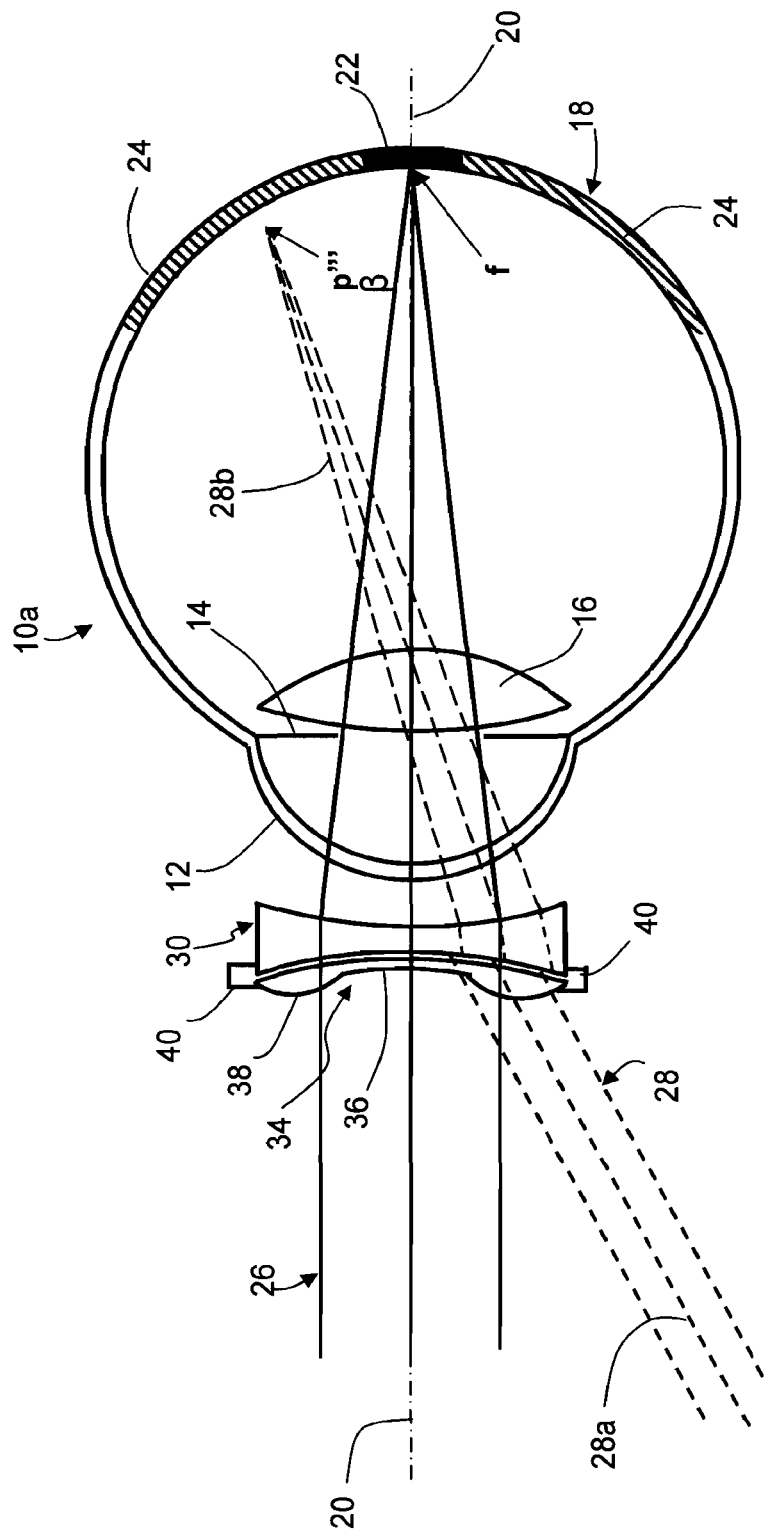
FIG. 5 is a similar diagram to that of FIG. 2 but illustrates the use of an add-on lens and a normal spectacle lens as a combined anti-myopia lens.

FIG. 5 shows the conversion of conventional spectacle lens 30 in FIG. 3 to an anti-myopia lens with the same effect as contact lens 32 by the addition of an add-on lens 34. Lens 34 has a plano central optic zone 36 that does not affect the central refractive power of base spectacle lens 30 so that central beam 26 can still be brought to focus at point f on the fovea of central retina 22. However, add-on lens 34 has an annular a peripheral refractive zone 38 with positive power that, despite the negative power of lens 30, generates sufficient peripheral myopic defocus to bring off-axis beam 28 to focus at point p''' in front of peripheral retina 24 (as in the case of contact lens 32, FIG. 4). Add-on lens 34 can be attached by mechanical clips 40 to base lens 30 (or to a spectacle frame, not shown), or it may be attached by a suitable adhesive.

Those skilled in the art will appreciate that there are known ways in which the refractive powers of the different zones of multi-zone artificial lenses can be measured in different quadrants, and in which the peripheral and central focal points of aided and un-aided eyes can be determined. International patent applications WO/2008116270 and PCT/AU2008/000434 by Erhmann et al respectively disclose techniques for mapping the refractive power of lenses and the eye at large peripheral angles.

The extensive surveys of youth in Australia and China that we have conducted in which we measured peripheral refractive error at 30 degrees (incident) in the nasal, temporal and superior quadrants confirmed that most (but not all myopes) have hyperopic defocus, but the amount was not as great as anticipated and did not increase as dramatically as expected for high myopes. Data from the myopic eyes included in these surveys has been condensed into the graphs or scatter charts of FIGS. 6-11 in which the refractive power of an eye is measured in terms of the spherical equivalent, and in which all peripheral measurements were made at 30 degrees (incident) in various quadrants. These graphs can be summarized as follows.

Figure 6:
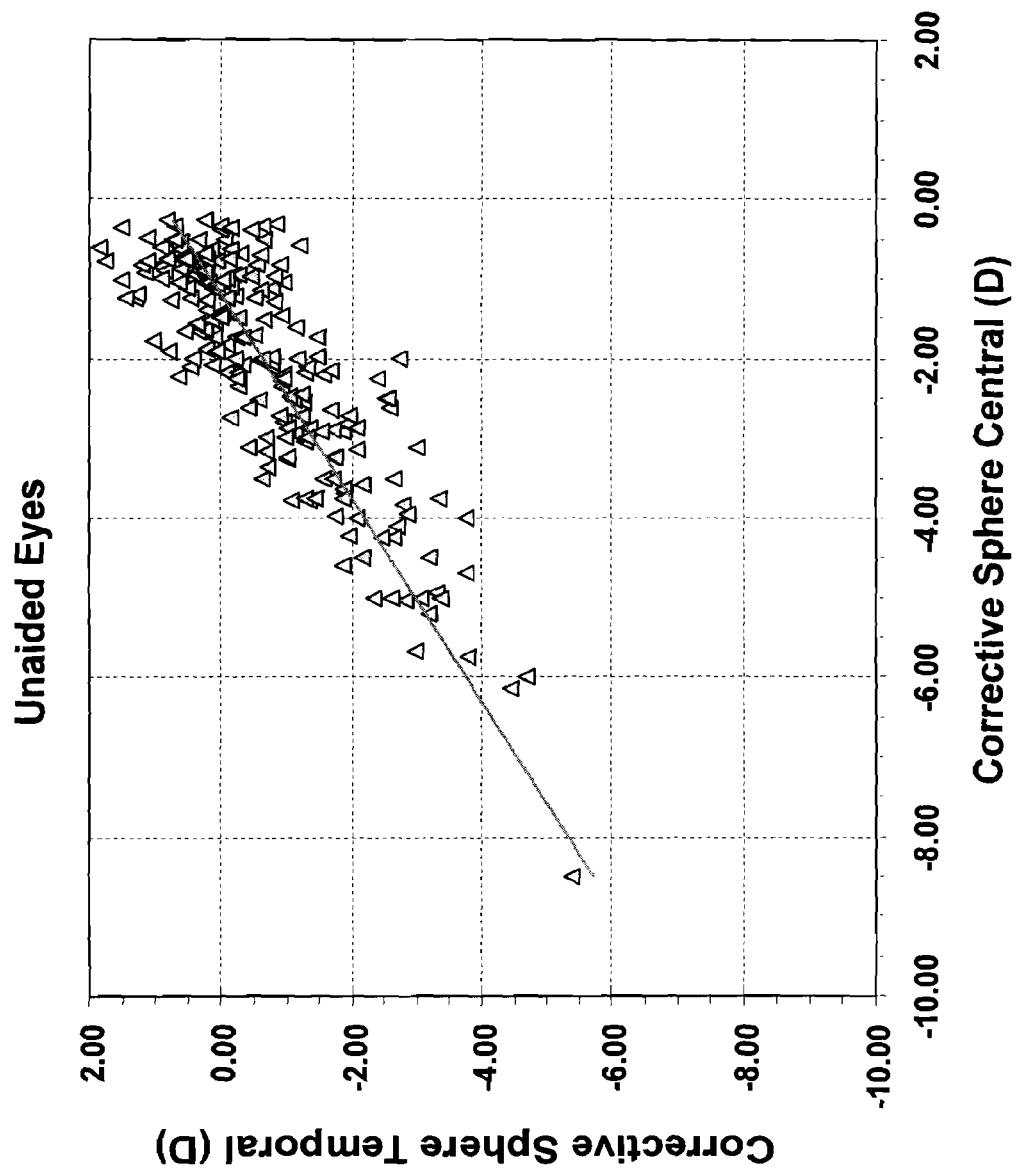
FIG. 6 is a scatter plot of spherical equivalent corrective power needed for peripheral rays in the temporal retina against central spherical equivalent corrective power of unaided eyes obtained from a large survey of youthful Australian and Chinese myopes.

FIG. 6 plots peripheral corrective refractive power (as spherical equivalent) of the surveyed eyes at 30 degrees in the temporal quadrant against central (on-axis) corrective refractive power (also as spherical equivalent), indicating a generally linear relationship. It will be seen that there is a 3 D spread in peripheral focus for mild myopes (better than −2 D), with most eyes exhibiting hyperopic (relative) defocus in the periphery. Those exhibiting hyperopic defocus would be considered to be a much greater risk for progressive myopia than those with myopic defocus. Similar results are evident for measurements of corrective peripheral powers in the nasal and superior quadrants—FIGS. 7 and 8 respectively—but with a significantly greater spread of corrective peripheral powers, especially in the superior quadrant.

Figure 7:
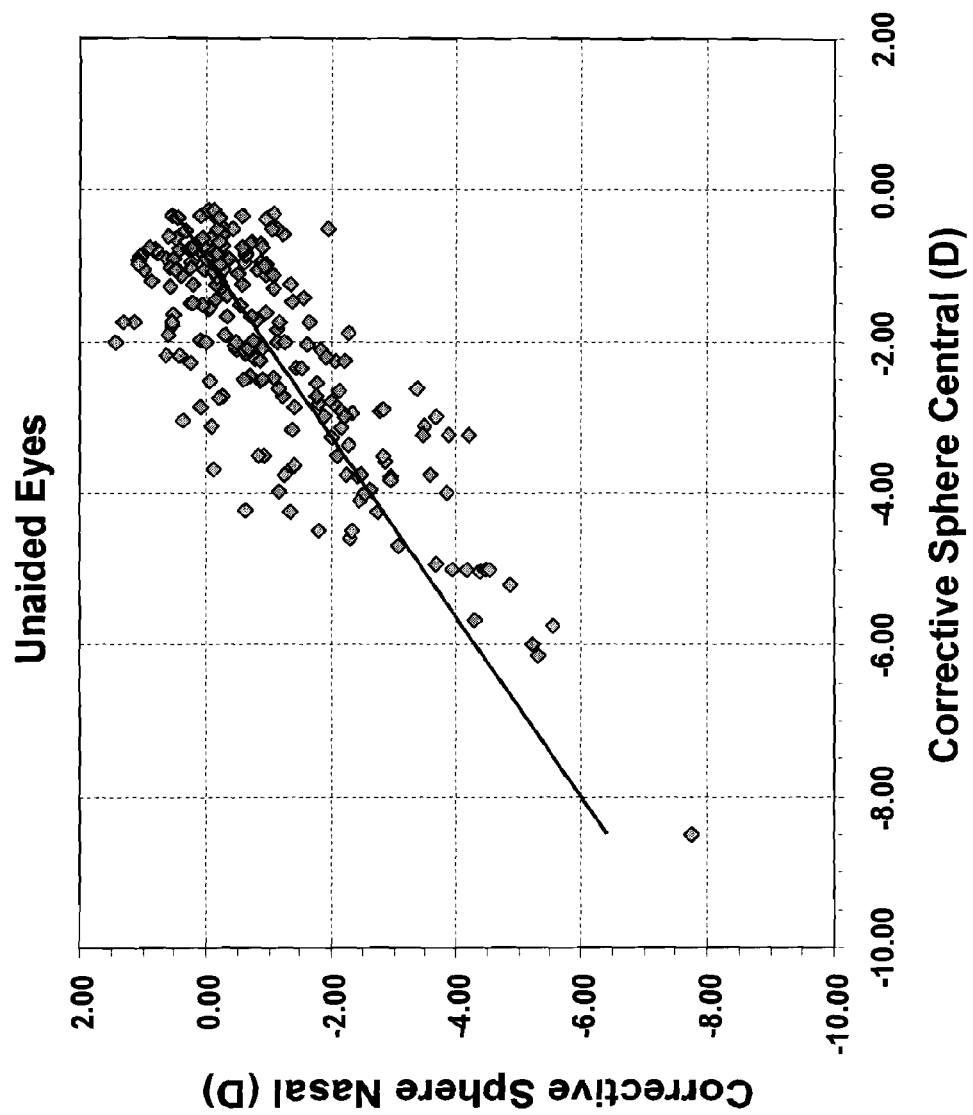
FIG. 7 is a scatter plot of spherical equivalent corrective power for the peripheral nasal retina quadrant against central spherical equivalent corrective power obtained from the survey of FIG. 6.
Figure 8:
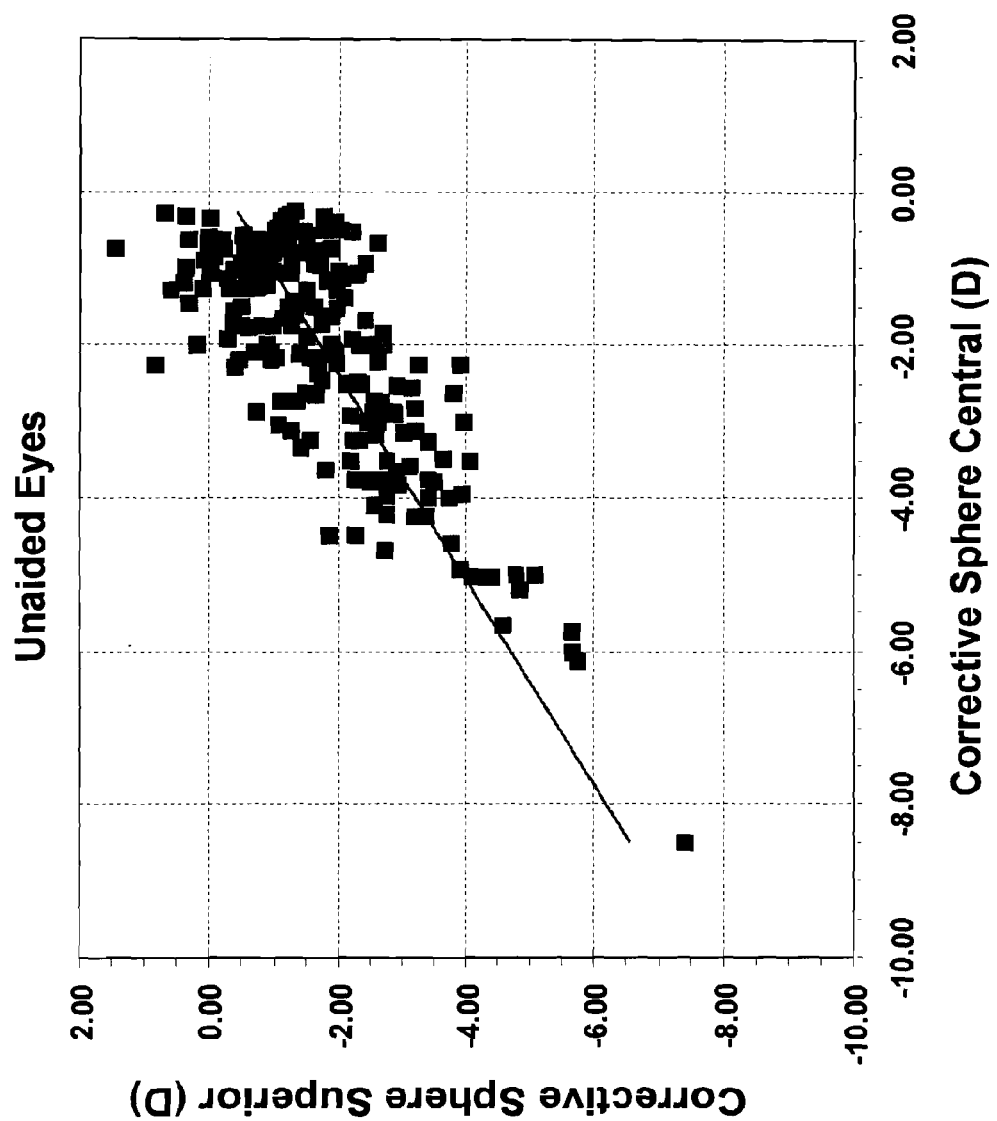
FIG. 8 is a scatter plot of spherical equivalent corrective power for the peripheral superior retina quadrant against central spherical equivalent corrective power obtained from the survey of FIGS. 6 and 7.
Figure 9:
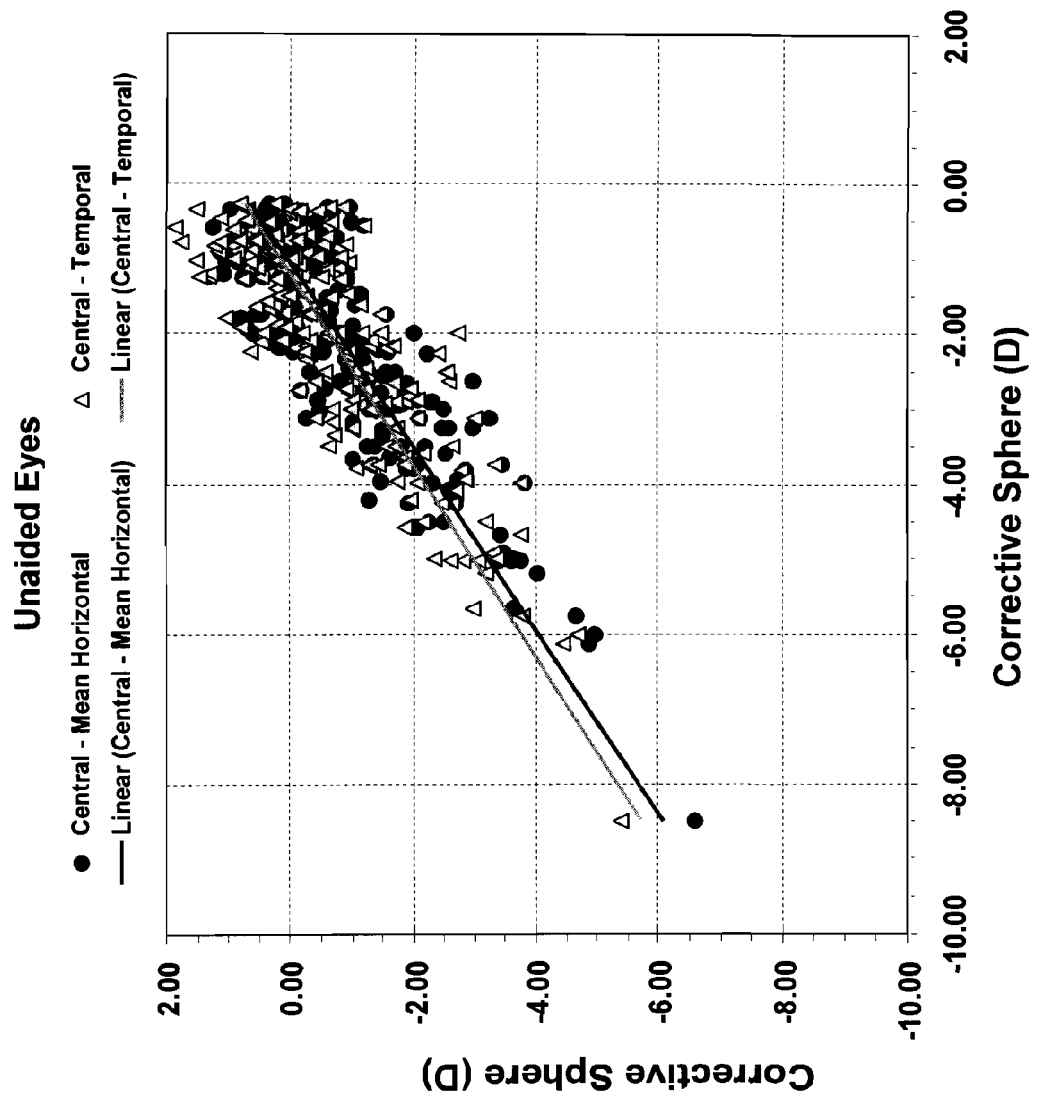
FIG. 9 is a scatter plot of central corrective power vs. mean horizontal peripheral corrective power and central corrective power vs. temporal peripheral corrective power, with best-fit linear regression lines shown for each, obtained from the survey of FIGS. 6 and 7.
Figure 10:
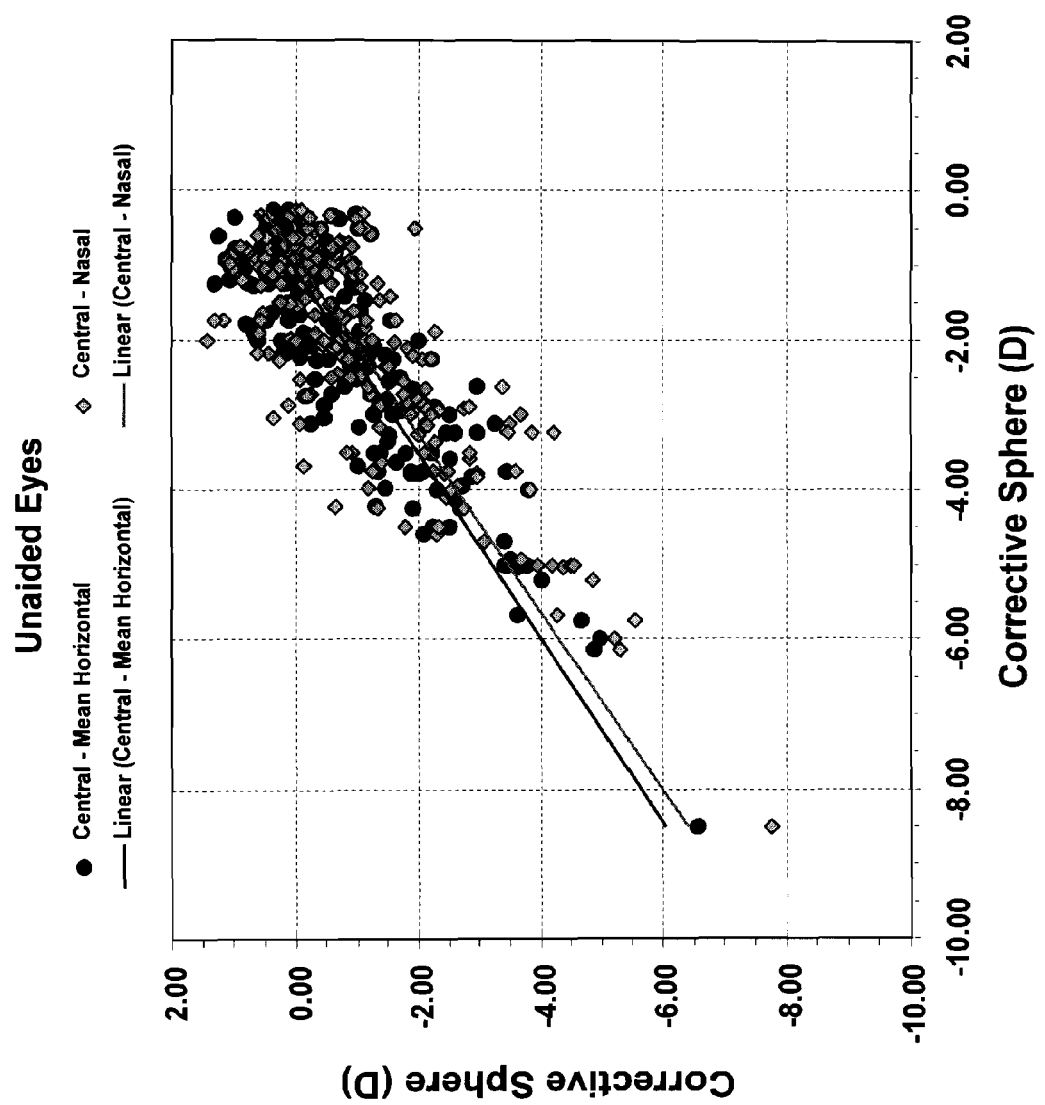
FIG. 10 is a scatter plot of central corrective power vs. mean horizontal corrective peripheral power and central corrective power vs. nasal quadrant corrective power, with best-fit linear regression lines shown for each, obtained from the survey of FIGS. 6 and 7.
Figure 11:
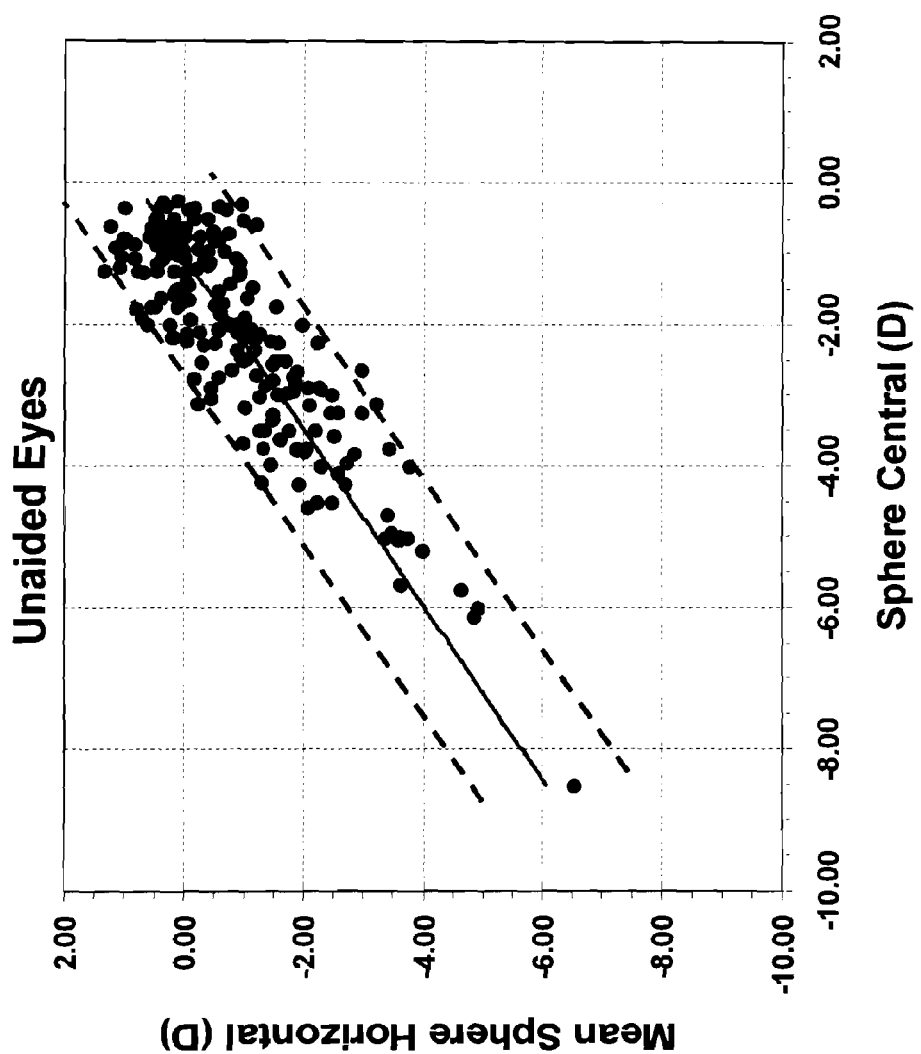
FIG. 11 is a scatter plot of mean horizontal corrective power against spherical corrective central power, obtained from the survey of FIG. 6.

FIGS. 9 and 10 present the corrective temporal and nasal power data of FIGS. 6 and 7. FIG. 9 plots corrective central vs. corrective mean horizontal power and corrective central vs. corrective temporal power, with best-fit linear regression lines shown for each. FIG. 10 plots corrective central vs. corrective mean horizontal power and corrective central vs. corrective nasal power, with best-fit linear regression lines shown for each. Finally, if the mean corrective horizontal power is plotted against the corrective spherical central power, as in FIG. 11, it will be seen that almost all of the survey population fall within a 3 D spread.

Clearly, this data supports the basis of the present invention; namely, that the peripheral power of anti-myopia lenses for normal myopes can be pre-set according to central power without peripheral defocus exceeding 3 D, thus avoiding the need to measure peripheral refractive error in the eye and prescribe customized lenses to both correct central refractive error and to appropriately control peripheral refraction for therapeutic purposes. Furthermore, the data can be reduced to useful look-up tables or rules of thumb that correlate the median sphere difference between central and peripheral power for rotationally symmetrical lenses (as in FIG. 12) or for rotationally asymmetric lenses having different temporal and nasal powers (as in FIG. 13).

Referring more specifically to FIG. 12, the left hand column [Central Refractive Error (D)] lists measured central refractive error in increasing increments of +0.25 D up to +6.00 D for the unaided eyes of the surveyed population. The second column from the left [Median Peripheral Refractive Error (D)] reports the measured median peripheral refractive error at 30 degrees (incident). Thus, −0.25 D myopes (those with a central refractive error of +0.25 D) were found, on average, to be −0.71 D hyperopic periphery and −5 D myopes of the population (those with a central refractive error of +5.00 D) were found, on average, to be +2.83 D myopic in the periphery. The third column [Median Script (Survey) Cent/Periph.] of the table of FIG. 12 indicates the absolute central and the peripheral defocus (respectively) of a customized prescription lens appropriate, on average, for the part of the surveyed population having the corresponding central and peripheral refractive errors indicated in the first two columns of FIG. 12. Thus a −0.25 D myope (with a +0.25 measured central error) requires a lens with a corrective central power of −0.25 D and a peripheral defocus of +0.96 D to (i) provide both good central vision and (ii) bring the peripheral focus (at 30 degrees incident) in front of the retina so as to substantially eliminate the stimulus for excessive eye growth. Similarly, a −5.0 D myope requires a corrective central power of −5.00 D and a peripheral defocus of +2.17 D for good vision and to substantially eliminate the stimulus for eye growth. Thus, the third column of FIG. 12 defines a pre-manufactured set, kit or stock of anti-myopia lenses with minimal pre-set peripheral powers. Conveniently, these lenses can be rotationally symmetric.

The two-part fourth column [Add Stepped Peripheral Power/Defocus to Lens] of the table of FIG. 12 indicates mild and high treatment options (levels of peripheral defocus) that may be used to provide corresponding medium and high levels of corrective stimulus for reducing eye growth. The 'mild' option adds +1.00 D, +1.50 D, +2.00 D and +2.50 D in four discrete steps of peripheral defocus, which increase the level of defocus over the minimal-treatment lenses of the third column of FIG. 12, while the 'high' level adds +1.50 D, +2.00 D, +2.50 D and +3.00 D in four steps of peripheral defocus. The use of steps in peripheral defocus (ie, where multiple lenses with the same central power have difference peripheral powers) is intended to simplify understanding and prescription by patients, clinicians and manufacturers. The lenses of the two-part fourth column of FIG. 12 are also conveniently rotationally asymmetric.

Referring more particularly to FIG. 13, the table of this Figure provides information useful in the case of manufacturing rotationally asymmetric lenses having different temporal and nasal powers. The left hand column [Central Refractive Error (D)] again lists increments of measured central refractive error in increasing increments of +0.25 D up to +6.00 D (for −0.25 D to −6.0 D myopes). The second column from the left [Median Temporal Refractive Error (D)] reports the median measured temporal refractive error for those of the surveyed population having the corresponding increment of measured central refractive error listed in the left hand column of FIG. 13. The third column from the left [Median Nasal Refractive Peripheral Error (D)] reports the measured median nasal refractive error for subjects having the corresponding central refractive error listed in the left-most column. It is noted that the surveyed population were somewhat more hyperopic in the temporal retina than in the nasal retina, suggesting that it might be advantageous to use the temporal retina measurements.

The fourth column [Median Script (Survey) Cent/Temporal] of the table of FIG. 13 can be regarded as defining a set of asymmetric anti-myopia lenses with minimal therapeutic power applied in the temporal quadrant of the retina, the second powers in the column being peripheral defocus in that quadrant. It is to be noted that the lenses will have the peripheral defocus applied to their nasal quadrants to affect the temporal retinal quadrant. Similarly, the fifth column [Median Script (Survey) Cent/Nasal] of FIG. 13 can be regarded as defining a set of asymmetric anti-myopia lenses with minimal therapeutic power applied to the nasal quadrant of the retina. Again, it is to be noted that the lenses of the set of the fifth column will have the peripheral defocus applied to their temporal quadrants to affect the nasal retinal quadrant.

The split sixth column [Added Stepped Peripheral Power] of the table of FIG. 13 indicates steps of peripheral defocus that can be used to modify peripheral defocus of the sets of lenses of the fourth and fifth columns. As shown, the column entitled "Temporal Chosen Power/Defocus" applies the peripheral defocus to the lenses of the 'temporal set' in four discrete steps, +1.5 D, +2.0 D, +2.5 D and +3.0 D to the temporal corrective power, while the "Nasal Chosen Power/Defocus" (right hand column) applies the peripheral defocus to the lenses of the 'nasal set' in three distinct steps, +1.0 D, +1.5 D and +2.0 D. Again, It should be noted again that, when considering lens design, it is the nasal and temporal quadrants (respectively) of the lenses to which the peripheral defocus is applied to effect the desired changes in the peripheral temporal and nasal quadrants of the retina. The lenses of the two-part fourth column of FIG. 13 [Add Stepped Peripheral Power] are, of course, rotationally asymmetric.

Figure 14:
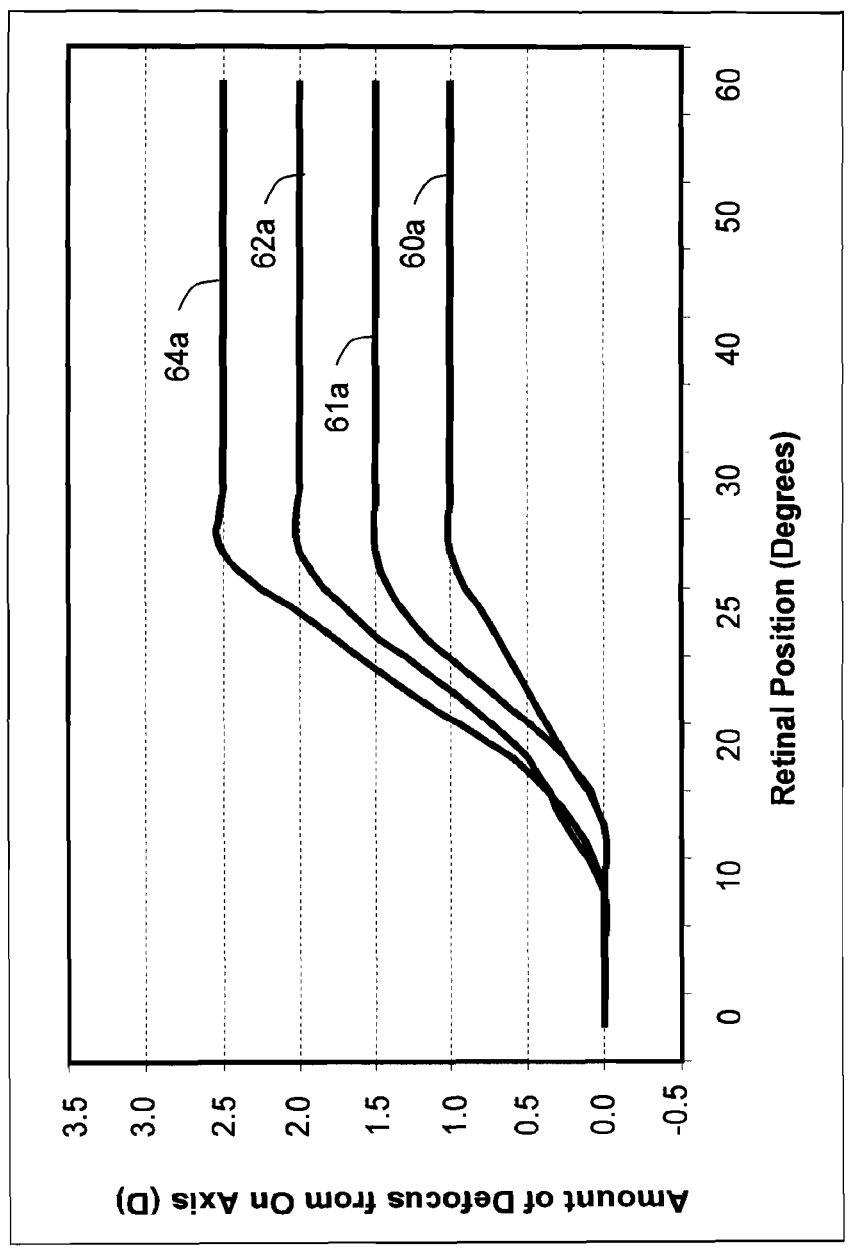
FIG. 14 is a graph showing peripheral defocus power curves of four exemplary contact lens designs that are consistent with the "Mild" prescription option of the table of FIG. 12.

FIG. 14 illustrates the relative power curves for each of the four steps of peripheral defocus of the contact lenses designed according to the 'Mild' option of FIG. 12 (fourth column). The maximum peripheral defocus of the lenses of this subset or option is set at 2.5 D. The reference numerals (60a, 61a, 62a and 64a) applied to the power curves are used in describing the two part trial kit of FIG. 15 below.

Figure 15:
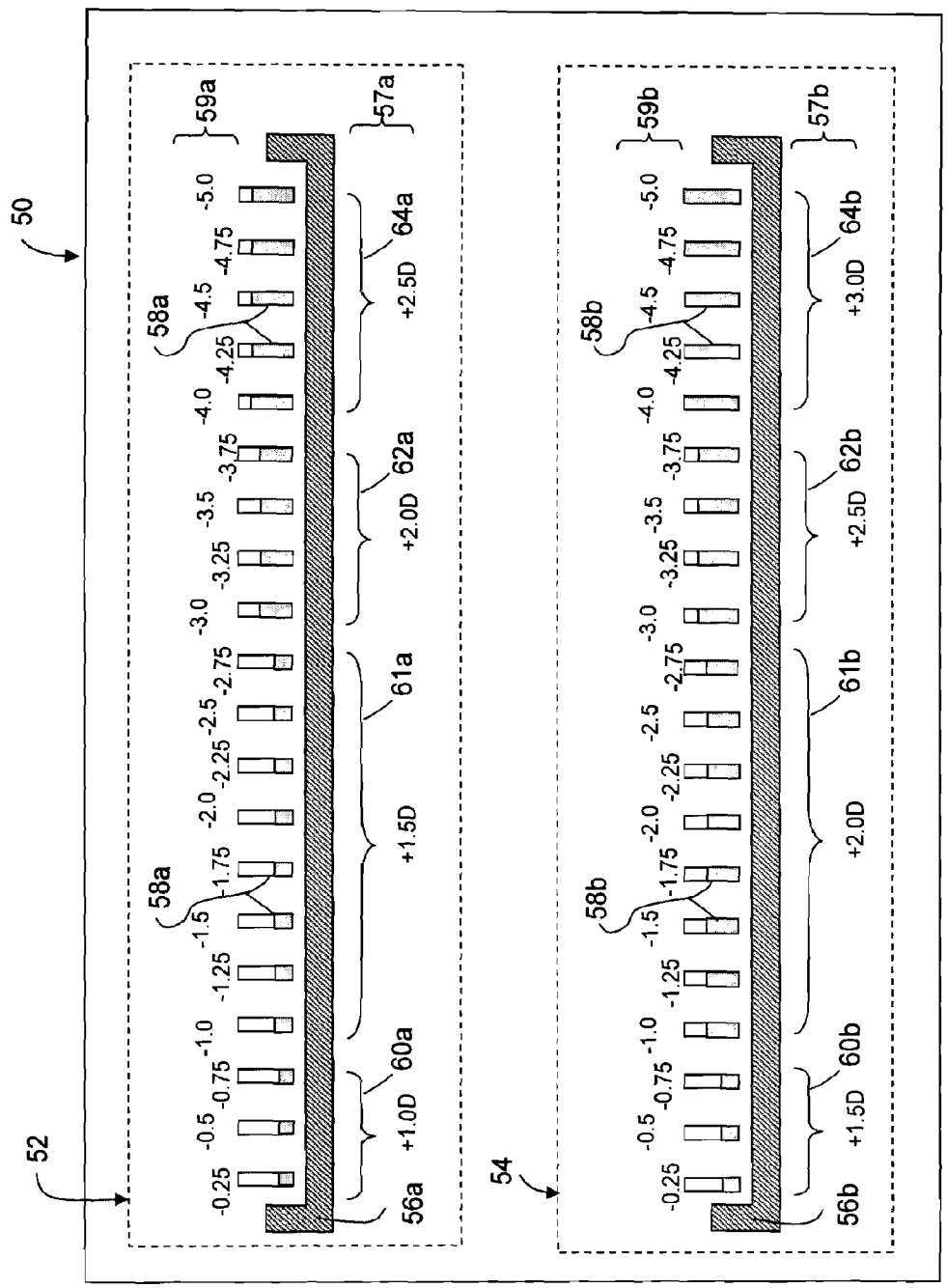
FIG. 15 is a diagrammatic representation of a two part trial kit of lenses suitable for use by a practitioner for both correcting myopia and inhibiting the progression of myopia in patients.

FIG. 15 is a diagrammatic representation of a two part trial or prescribing lens kit or set suitable for practitioners, which can be substituted for conventional kits at little extra cost and can comprise a kit or set of finished trial spectacle lenses or a kit or set of trial or dispensing contact lenses. This Figure can be viewed as a diagrammatic plan view of a single drawer or tray 50 in which lenses are arranged in two arrays or parts 52 and 54 on a single level, or it can be viewed as a diagrammatic sectional elevation of a cabinet 50 that has two drawers or parts 52 and 54, one above the other. The lenses of part 52 conform to those set out in the 'Mild' peripheral power column (second from right) while the lenses of part 54 conform to those set out in the 'High' peripheral power (far right) of the tabulation of FIG. 12. Thus, kit or set 50 has double the minimum number of lenses need for a kit covering 'normal myopes' up to −5.00 D. In this example, the lenses 58a and 58b are each packaged in a suitable sachet (not separately illustrated).

In FIG. 15, part 52 comprises a compartmented container 56a accommodating 20 different lenses 58a covering −5 D in −0.25 D increments of central corrective power while part 54 comprises a compartmented container 56b also with 20 lenses 58b covering −5 D of negative central power in −0.25 D increments. The respective increment of central power is written above lenses 58a of part 52 as indicated by bracket 59a and the central powers of lenses 58b of part 54 are similarly indicated at 59b. The peripheral defocus of lenses 58a are collectively indicated by bracket 57a and the peripheral defocus of lenses 58b are collectively indicated by brackets 57b. Containers 56a and 58a can be differently color-coded, for example container 56a may be yellow and 58a may be red, and all the lens sachets of each container are similarly differentiated using the same color codes—as well as bearing both the central power and the peripheral defocus of the enclosed lens(es), to minimize the chance of a lens sachet being place in the wrong part of kit 50 or the chance of the wrong sachet/lens being selected for trial or use. For convenience of use, lenses 58a and 58b are arrayed in their respective containers 56a and 56b according to their increments of central power, though this need not be done in the linear fashion shown in FIG. 15. The lenses 58a of part 52, in this example, together include four steps of peripheral power and, thus, form four sub-sets of lenses, indicated by brackets 60a, 61a, 62a and 64a. (The designs for these lenses are those of FIG. 14.) The peripheral defocus of each sub-set is diagrammatically indicated by the height of the shaded portion of each lens and by the power number having a plus sign associated with the respective brackets. Thus sub-set 60a has three lenses 58a each having a peripheral defocus of 1.0 D, sub-set 61a has 8 lenses each with a peripheral defocus of 1.5 D, sub-set 62a has 4 lenses each with a peripheral defocus of 2.0 D and sub-set 64a has five lenses 58a each with a peripheral power of 2.5 D. Similarly, part 54 has four sub-sets 60b, 61b, 62b, and 64b having three, eight, four and five lenses 58b with peripheral defocus steps marked +1.5 D, +2.0 D, +2.5 D and +3.0 D respectively.

Lens kit or set 50 can be used in the following manner. The practitioner makes a normal estimate or measurement of central refractive error of the patient's eyes using existing equipment and techniques employed for the prescription of conventional corrective lenses, and reviews the patient history to judge whether the patient is likely to suffer from progressive myopia. If not, a lens from part 52 of kit 50 with the appropriate corrective central power is selected and tried; if so, a lens from part 54 is selected and tried. If the patient is not satisfied with the acuity of central vision provided by the selected lens, the lens with the next adjacent central power from the same part of the kit is tried. If a patient who is trial-fitted with a lens from part 54 finds the peripheral blur excessive, the lens with the same central power in part 52 of the kit can be substituted. In either case, the clinician can be highly confident that the selected lens will act to inhibit the progression of myopia in the patient to some degree by bringing the peripheral focus onto or in front of the peripheral retina to provide the desired stimulus for inhibiting further eye growth. Where kit 50 is one of contact lenses, it can be used to dispense finished lenses to the patient or to make the appropriate order for supply from a wholesaler or manufacturer. Where kit 50 is one of finished trial spectacle lenses and the clinic has its own lens finishing grinding and/or polishing facility, it may supply finished lenses to the patient; otherwise, orders for such lenses are placed with manufacturers in the conventional manner.

Figure 16:
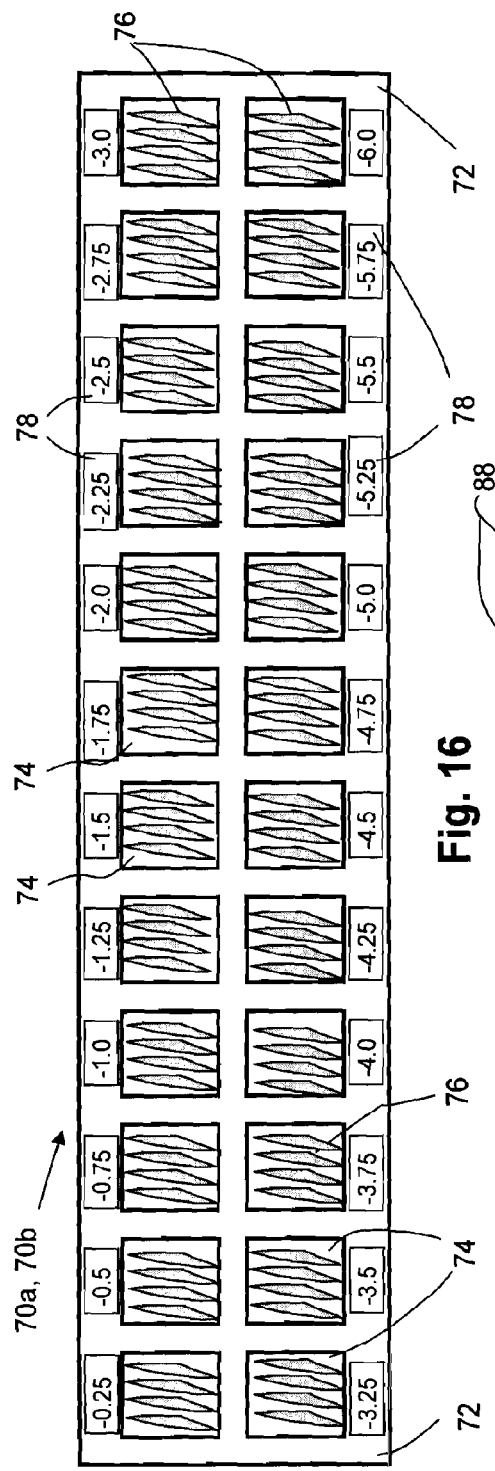
FIG. 16 is a diagrammatic representation of a trial and dispensing kit, set or stock of contact lenses.
Figure 17:
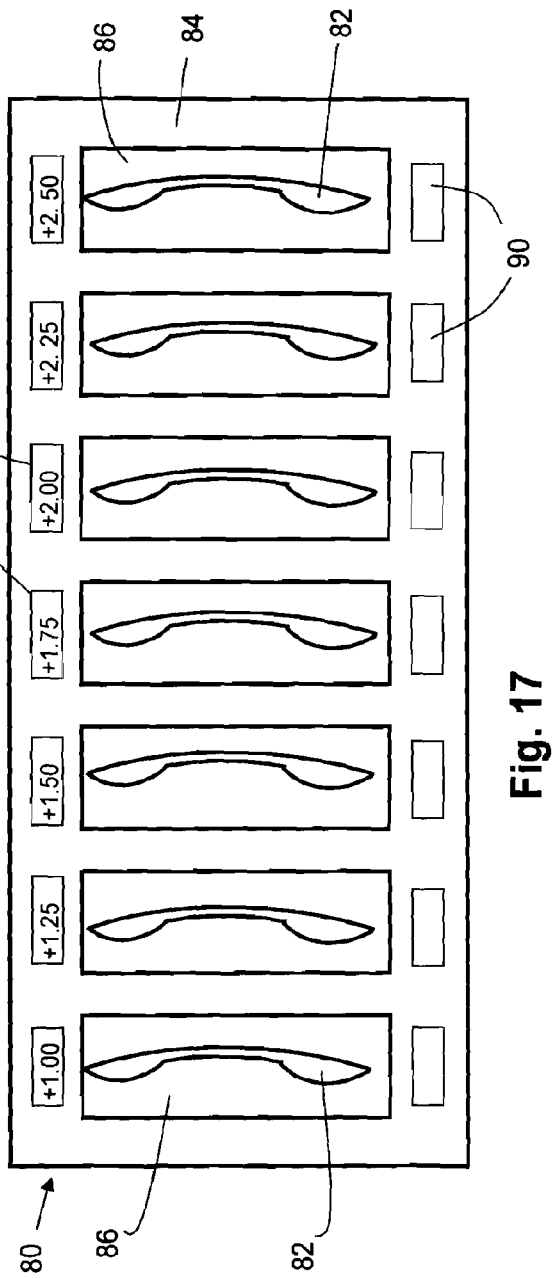
FIG. 17 is a diagrammatic representation of a small kit of add-on spectacle lenses.

Two further types of sets, kits or stocks formed in accordance with the principles of this invention are illustrated in FIGS. 16 and 17. Furthermore FIG. 16 illustrates two different contact lens kits, sets or stocks 70a and 70b, each comprising a box, tray or drawer 72 having a plurality of compartments 74, each of which stores multiple sachets 76 of contact lenses (not separately shown) having the same central corrective power. For convenience, only four sachets 76 are shown in each compartment 74. The central power of the lenses in each compartment 74 is written above or below each compartment on labels 78. It will be seen that the central power of the lenses ranges from −0.25 D to −6.0 D in 0.25 D increments.

In kit, set or stock 70a, the sachets 76 in each compartment 74 not only have the same central power but have the same peripheral power; that is, the lenses in each compartment are identical so that they can serve as a combination trial kit and supply stock. Each sachet is clearly identified with the central corrective power and, while the peripheral power need not be included in this example, it is preferable that all the sachets of the kit are coded (for example by color) to show that they belong to one consistent series or kit type. The peripheral powers of the lenses in the compartments conform to the median power of the surveyed population for the respective central corrective powers according to the third column of FIG. 12. That is, no two lenses of the stock or kit 70a with different central powers have the same peripheral power; conversely, each central power is associated with a unique peripheral power. The lenses of kit or stock 70a therefore have the minimum positive therapeutic effect.

In kit, set or stock 70b, lenses with multiple therapeutic levels but the same central power are housed in each compartment 74, the label 78 of the compartment indentifying the respective central power of the lenses therein. Each sachet 76 of each compartment is coded to indicate the level of therapeutic effect and preferably has written identification of central power, peripheral power and treatment level. In this example, sachets 76 with four different levels of treatment are contained in each compartment 74, the lowest being that of kit 70a described above and taken from the third column of FIG. 12, second lowest being taken from the second last column of FIG. 12, the second highest being taken from the second last column of FIG. 13 and the highest being taken from the last column of FIG. 13. This kit, set or stock of lenses is then used in essentially the same manner as kit or set 50 described with reference to FIG. 15, except that the clinician is now given a wider discretion to prescribe according to his or her assessment of the patient's propensity to progressive myopia from the patient history—which, of course, will include familial history of myopia.

The final example of the trial set or kit is a seven-lens trial set or kit 80 of add-on lenses 82 for spectacles diagrammatically illustrated by FIG. 17, set or kit 80 comprising a rack 84 with sections or troughs 86, which hold add-on lenses having plano central power and different steps/levels of peripheral power or defocus. In this case, sections 86 have labels 88 to indicate the step/level of added peripheral power or defocus, which is from +1.0 D to +2.5 D in 0.25 D increments and corresponds to the 'Mild Add' option of the table of FIG. 12 (except for the finer 0.25 steps) of peripheral defocus. Since the add-on lenses 82 of kit 80 may not all have a common base curve, or other kits like this with sets of lenses having different base curves may be used, it will be convenient for the base curve of each add-on lens to be identified additionally by labels 90. However, as in previous examples, it is also desirable to mark the lenses or their sachets (if provided) to identify the peripheral power and the base curve.

The manner of use of kit or set 80 is similar to that described for kit or set 50 (FIG. 15). The practitioner checks central refractive error of the patient's eyes, judges the patient's propensity for progressive myopia from patient history, selects an add-on lens with a level or peripheral defocus appropriate to the judged propensity and tries the selected add-on lens on the patient's habitual spectacle lens or on a semi-finished trial base lens with the appropriate central power. If the patient finds the peripheral blur excessive, an add-on lens with the next lower level of peripheral defocus is tried until patient acceptance is obtained. A final spectacle lens may then be ordered or finished using an in-house grinding and polishing facility. The ability to provide so many levels of peripheral defocus from a small set or kit of lenses is an obvious advantage.

Turning more specifically to the anti-myopia ophthalmic devices themselves, and more specifically to ophthalmic lenses such as contact lenses, as noted above the peripheral power may be presented in a peripheral power profile wherein the peripheral power changes with radial distance, such that the peripheral power profile exhibits the peripheral power values located at a determined distance from the central axis. Previously the peripheral power profile of ophthalmic lenses was left the same or adjusted to reduce spectacle distortion or improve central vision. Due to the lower visual acuity of the peripheral retina, correcting the peripheral refraction was not seen as significant improvement.

As mentioned above, the peripheral defocus of the lens is determined by the differential between the central power for the ophthalmic lens and the peripheral power at a particular point on the peripheral power profile. An ophthalmic device, according to the present invention, is contemplated to have a differential lens power (peripheral defocus of the lens) that is a function of the central sphere power. However, considerable individual variability in differential refraction (peripheral minus central) has been observed among both children and adults of comparable central refractive status. As a consequence, the use of an anti-myopia ophthalmic/contact lens with an average, single, peripheral defocus/differential lens power may overcorrect the peripheral retina in some myopes, but undercorrect the peripheral retina in other myopes, depending on the individual peripheral defocus of a particular eye. The optical effect for under-correction may be a residual amount of hyperopic defocus in the peripheral retina, which would also create a stimulus for axial eye growth and worsening myopia. On the other hand, the optical effect for severe overcorrection of the peripheral retina may be an excessive amount of myopic, peripheral defocus, which not only could hamper peripheral vision but also cause peripheral form vision deprivation resulting in further axial eye growth and myopia progression. Using an anti-myopia contact lens with an above-average, single, peripheral defocus/differential lens power such that in most progressing myopes peripheral hyperopia is converted to peripheral myopia would prevent under-correction in some myopes, but create severe over-correction in other myopes with the above-mentioned consequences.

In a series of lenses according to the present invention, each lens has a differential lens power (amount of peripheral defocus) targeted at the average relative peripheral refraction for a given central sphere power. A lens with a greater than average peripheral defocus can be produced. Alternatively, a lens with a lesser than average peripheral defocus can be produced. This means that while that peripheral defocus for the lens can be greater or lower than the determined average, the amount of peripheral defocus varies as a function of the particular central sphere power so as to produce lenses that adequately correct a variation in the level of peripheral refraction. In an alternative embodiment, ophthalmic lenses may be customized based on a particular individual's determined level of peripheral refraction. As such, after determining the particular individual's needed amount of peripheral defocus/differential lens power, customized ophthalmic lenses are manufactured.

The relationship between central power and peripheral defocus of the lens can be, at a minimum, a first order (linear) relationship such that the peripheral defocus increases as a constant function of the central sphere power for each lens. While a linear relationship fits the discovered refractive relationship between the central and peripheral refractions, this could be extended to higher order or non-polynomial relationships to produce a more refined non-linear relationship. The result is an increasing peripheral defocus from a minimum at low myopia (−0.25 D) to a maximum at high myopia (−30.00 D) or as limited by optical design constraints. This is unlike other optical corrections such as presbyopia where the loss of accommodation is not related to amount of myopia. For the correction of presbyopia there is no increase in additional power as a function of the refractive myopia.

This relationship provides a more precise induced peripheral refractive change than using a fixed peripheral defocus for the lens. This relationship is based on the experimental finding that an eye's central to peripheral refraction may increase with the amount of myopia. When applied to a power range of inventoried anti-myopia lenses the experimentally determined mean central to peripheral refraction would be used as the function to design the lens's optical peripheral defocus for each lens sphere power.

In additional study results on the peripheral refraction of the eye which were obtained in the CIBA Vision Research Clinic, it was shown that the most hyperopic refractive foci (the sphere meridian) of a myopic eye can vary from less than between approximately 0.25 D and 4.00 D (at −6.00 D, and even greater for higher minus power is expected) difference from central axis to 30 degrees off-axis. More desirably, at 30 degrees off axis, the range can be approximately between 0.25 D and 3.0 D, and even more desirably between approximately 0.25 D and 2.5 D. Between central axis and 40 degrees off-axis, that difference increases and can be approximately between 0.50 D and 6.00 D. Evaluation of optical designs of soft contact lenses where the peripheral defocus was more positive has shown that high (2.50 D) differential refractions can be corrected (see FIG. 20). However, the same peripheral defocus design worn on an eye with 0.75 D differential refraction overcorrects the peripheral refraction and produces obvious peripheral blur for the wearer.

Figure 18:
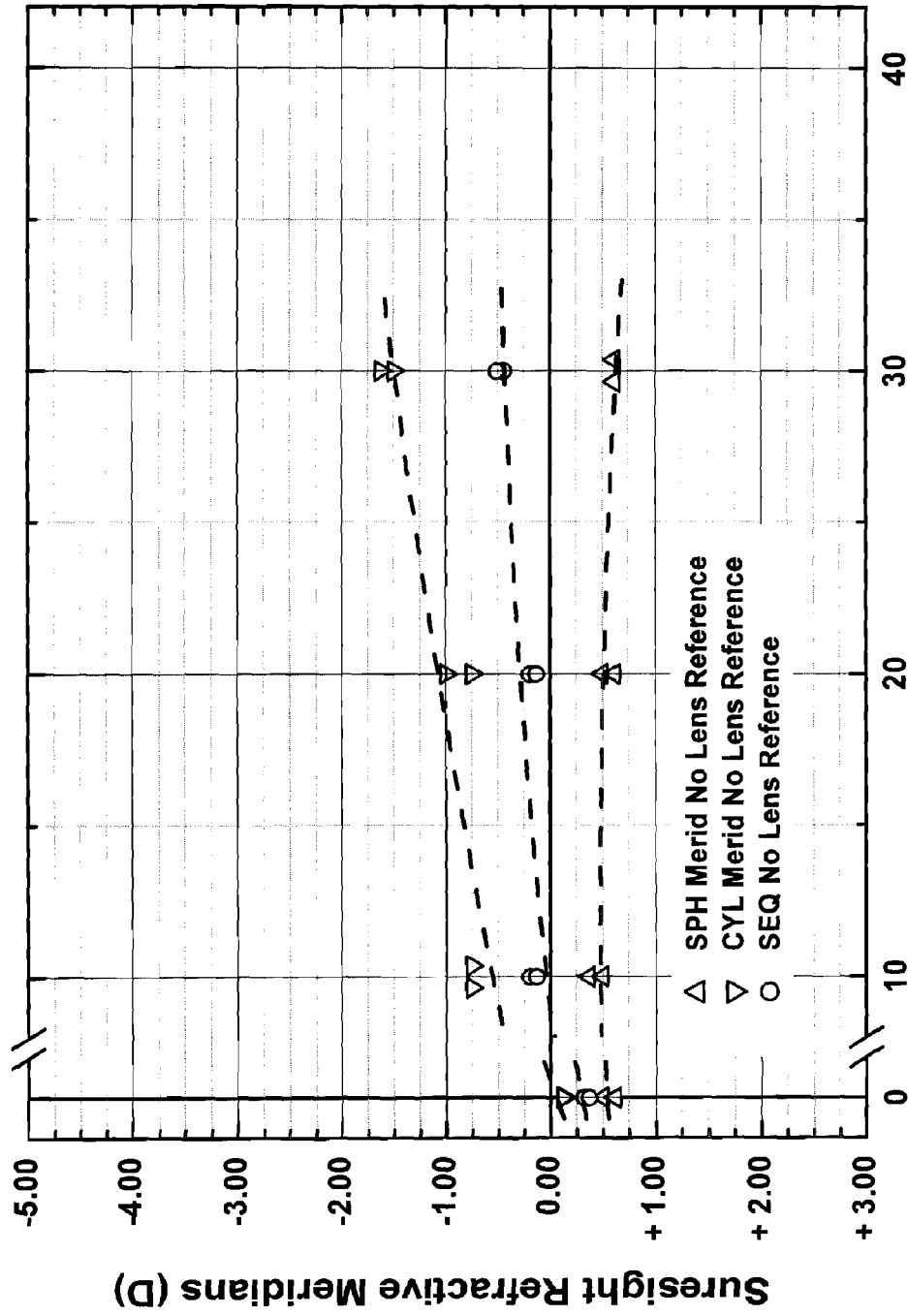
FIG. 18 represents the central and peripheral auto refraction of an eye which is emmetropic with power (D) in the y axis and offset (in degrees) from the central axis in the x axis.

FIG. 18 represents the central and peripheral auto refraction of an eye which is emmetropic. There is very little relative peripheral hyperopia (less than 0.50 D at 30 degrees) and in this particular case the relative peripheral hyperopia is −0.62 (at 30 degrees off axis) minus −0.62 D (at central axis), which is 0.00 D.

Figure 19:
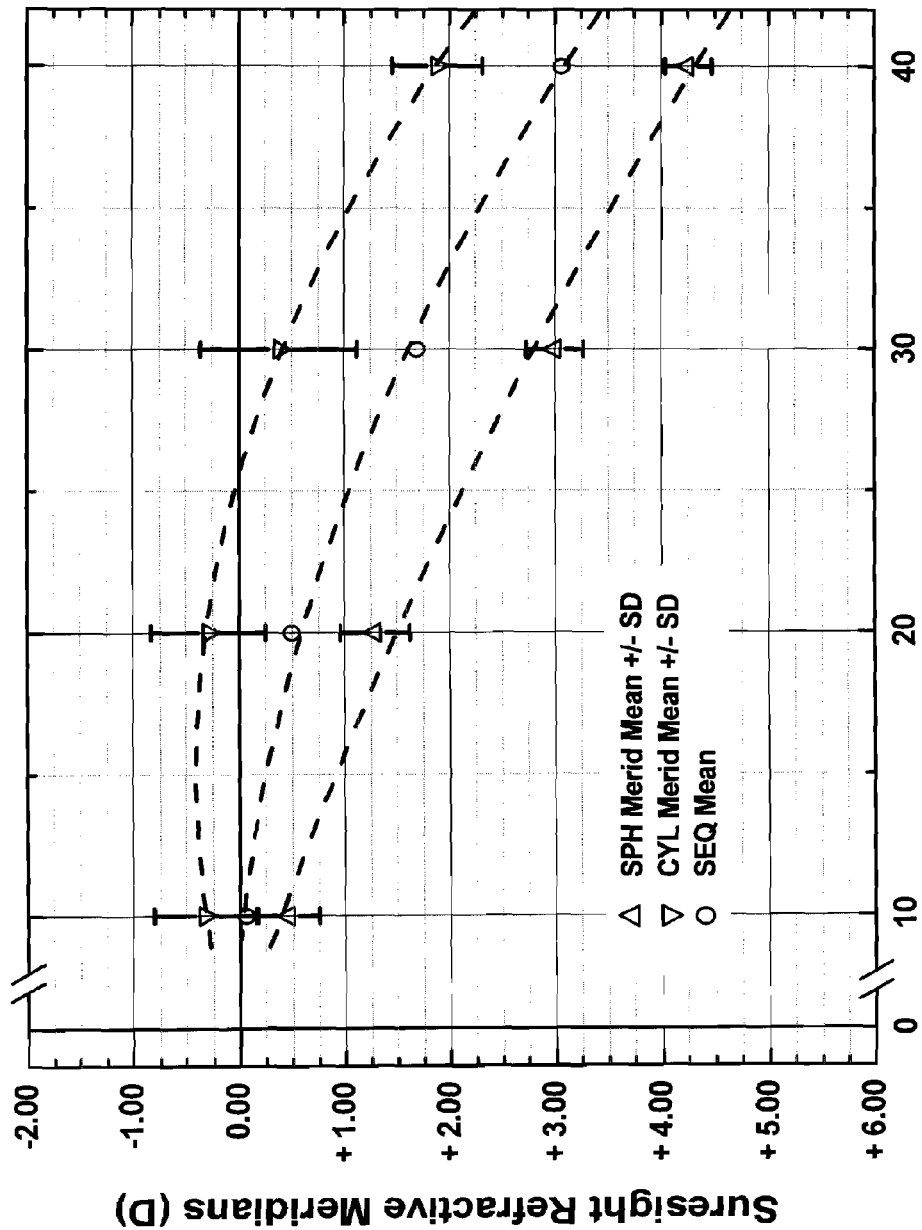
FIG. 19 shows the peripheral auto refraction of an eye which is highly (with a subjective central refraction of about −6.00 D) myopic with power (D) in the y axis and offset (in degrees) from the central axis in the x axis.

FIG. 19 represents the peripheral auto refraction of an eye which is highly myopic; in this case wearing a conventional soft contact lens for measurement purposes with an auto refractor. There is much more relative peripheral hyperopia (greater than 2.00 D at 30 degrees off axis) and in this particular case the relative peripheral hyperopia is 2.75 D (at 30 degrees off axis) minus 0.37 D (at ten degrees off axis), which is 2.37 D.

Figure 20:
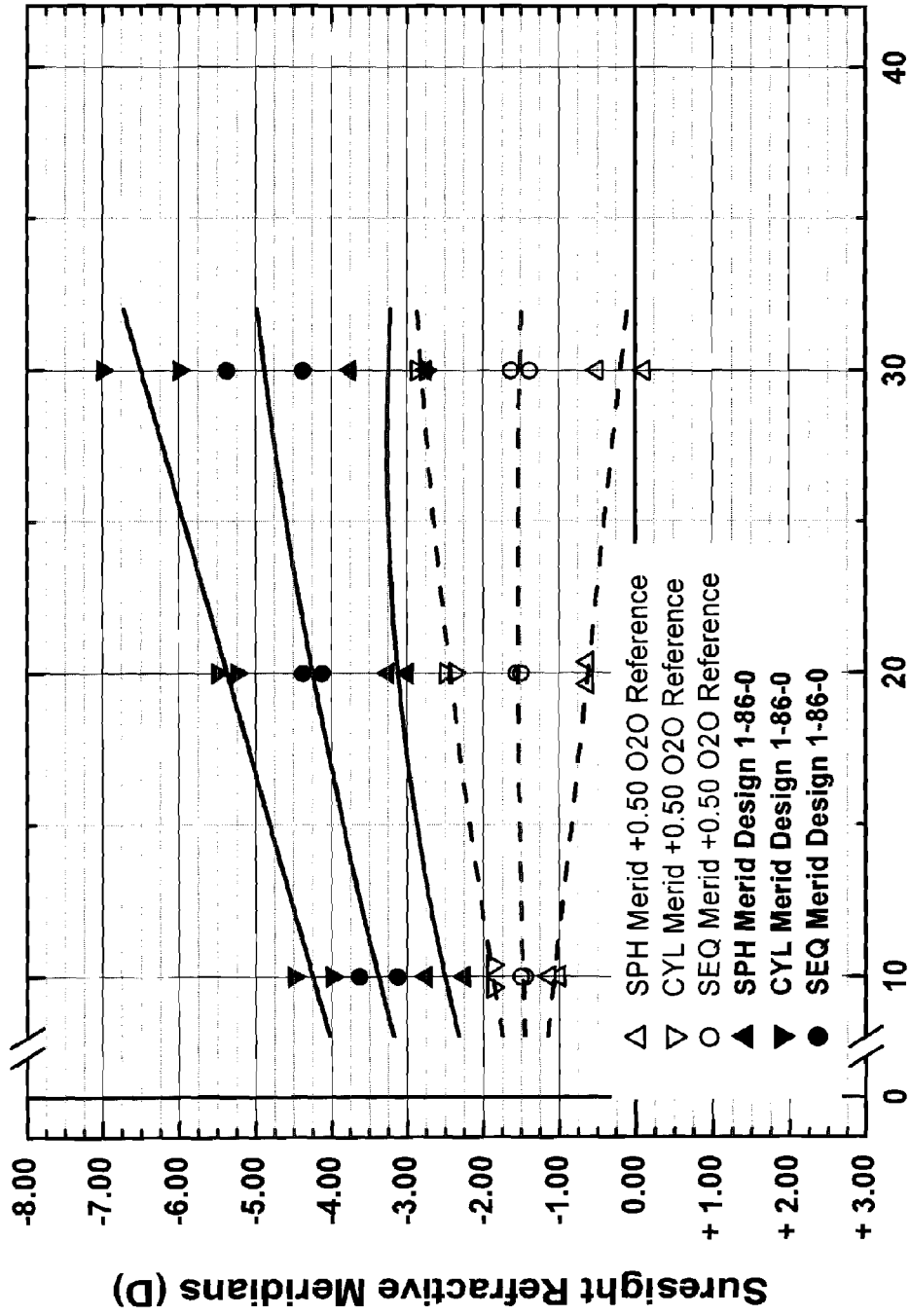
FIG. 20 shows the peripheral auto refraction of an eye myopic eye with a subjective central refraction of about −1.50 D and the peripheral auto refraction through a soft contact lens with a high peripheral defocus with power (D) in the y axis and offset (in degrees) from the central axis in the x axis.

FIG. 20 represents a myopic eye with a subjective central refraction of about −1.50 D. The relative peripheral hyperopia in this particular case is low at −0.25 D (at 30 degrees off axis) minus −1.00 D (at ten degrees off axis), which is 0.75 D. The additional refractive data was taken through a soft contact lens designed to correct high levels of relative peripheral hyperopia. The effect of this lens correcting the eye is now relative peripheral myopia and in this particular case the relative peripheral myopia is −3.25 D (at 30 degrees off axis) minus −2.50 D (at ten degrees off axis), which is −0.75 D. Along with the overall myopic shift of the auto refraction, this change in peripheral auto refraction was too much and caused subjective distortion of peripheral vision.

Figure 21:
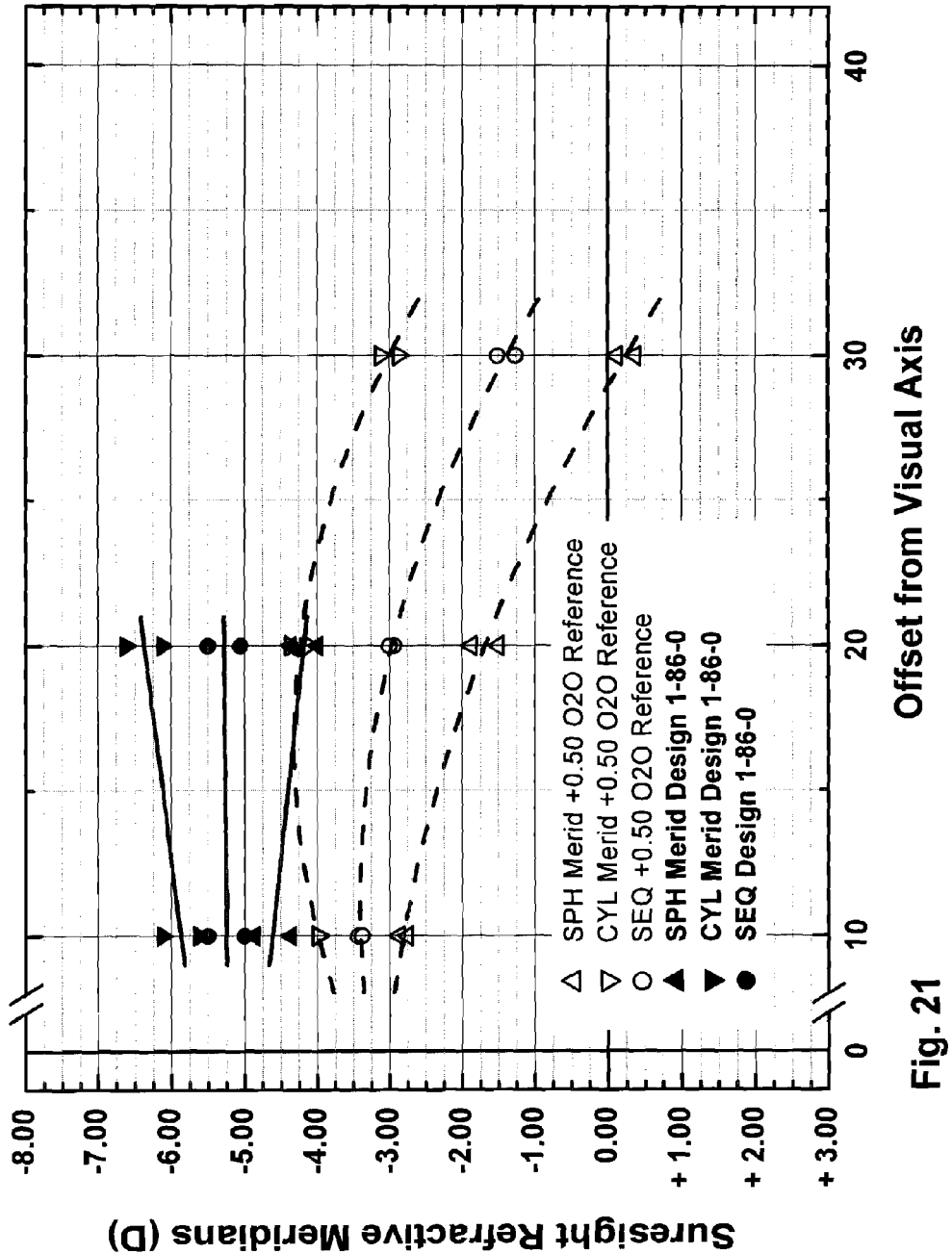
FIG. 21 shows the peripheral auto refraction of same highly myopic eye as in FIG. 19 and the peripheral auto refraction through a soft contact lens with a high peripheral defocus with power (D) in the y axis and offset (in degrees) from the central axis in the x axis.

FIG. 21 represents the peripheral auto refraction of the same highly myopic eye as in FIG. 19, in this case −6.00 D imaged through a −4.00 D correction lens for measurement purposes with an auto refractor. The additional refractive data was taken through the soft contact lens designed to correct high levels of relative peripheral hyperopia as used in FIG. 20. The effect of this lens correcting the eye is much less relative peripheral hyperopia, and in this particular case the relative peripheral hyperopia is −4.25 D (at 30 degrees off axis) minus −4.62 D (at ten degrees off axis), which is 0.37 D. Along with the lesser overall myopic shift of the auto refraction, this change in peripheral auto refraction was less and caused no subjective distortion of peripheral vision.

Figure 22:
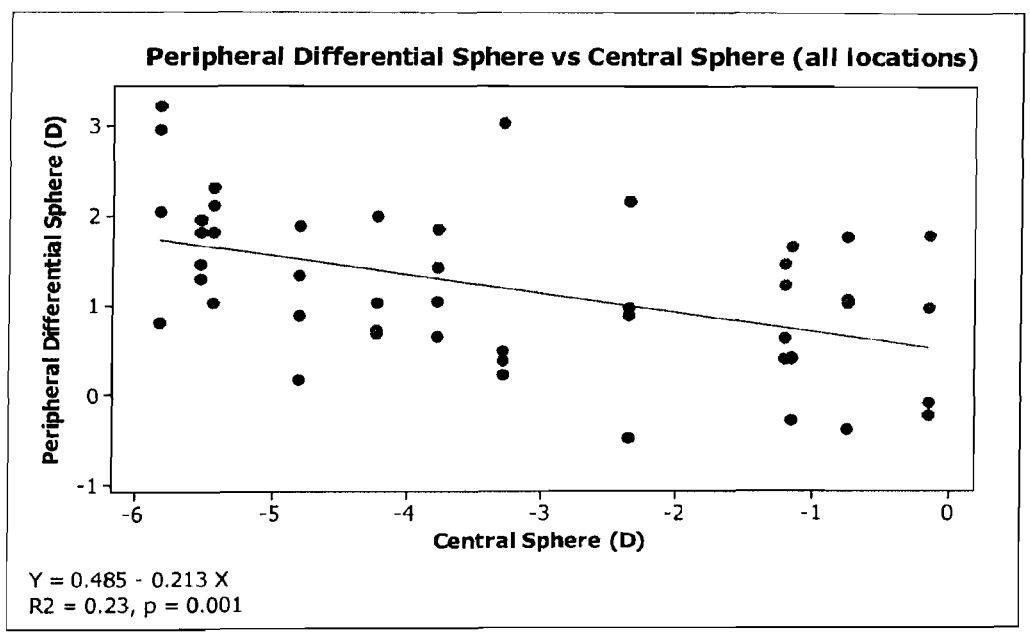
FIG. 22 shows the results of a study of Schmid in which the sphere power in minus cylinder notation was measured centrally and at 20 degrees in the nasal, temporal, inferior and superior retina with central sphere power (D) in the X axis and peripheral differential power (D) in the Y axis.

FIG. 22 represents the results of a study of Schmid in which the sphere power in minus cylinder notation was measured centrally and at 20 degrees in the nasal, temporal, inferior and superior retina with a Shin Nippon K5001 open-field auto-refractometer in both eyes of six young adult volunteers during cycloplegia. Plotting the relative peripheral refraction for sphere power (peripheral minus central sphere power) for each location vs. central sphere power revealed an inverse correlation. Statistical significance was reached for the mean of all four peripheral locations combined.

Figure 23:
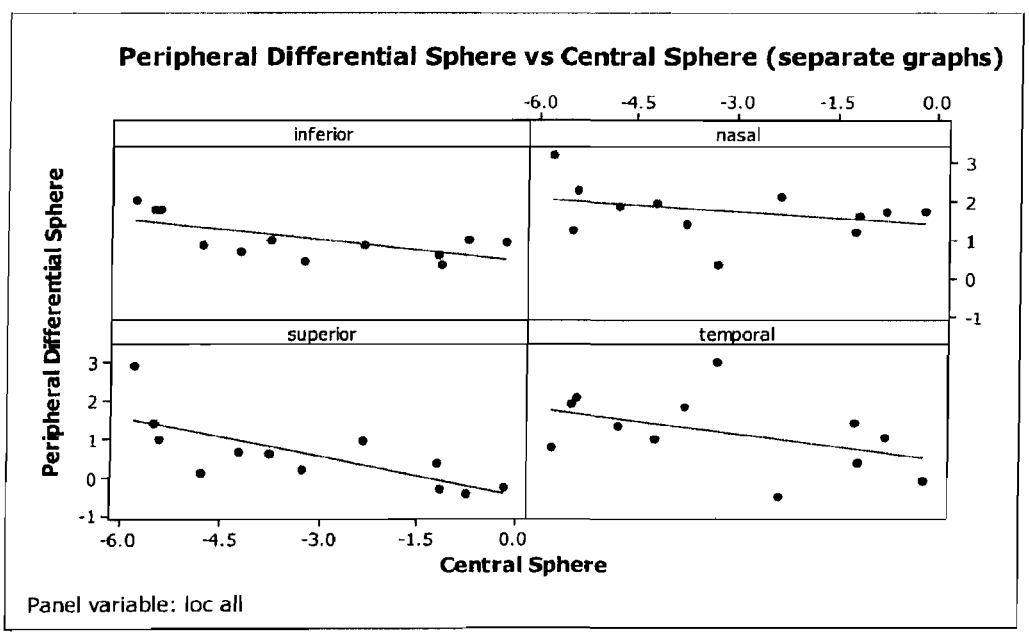
FIG. 23 shows more details on the study of Schmid and separates the nasal, temporal, inferior and superior data with central sphere power (D) in the X axis and peripheral differential power (D) in the Y axis.

FIG. 23 represents more details from the Schmid study. All four quadrants showed the same trend of increasing relative peripheral hyperopia with increasing central myopia. Individually, statistical significance was reached for the inferior and superior quadrants where the change is slightly larger.

Figure 24:
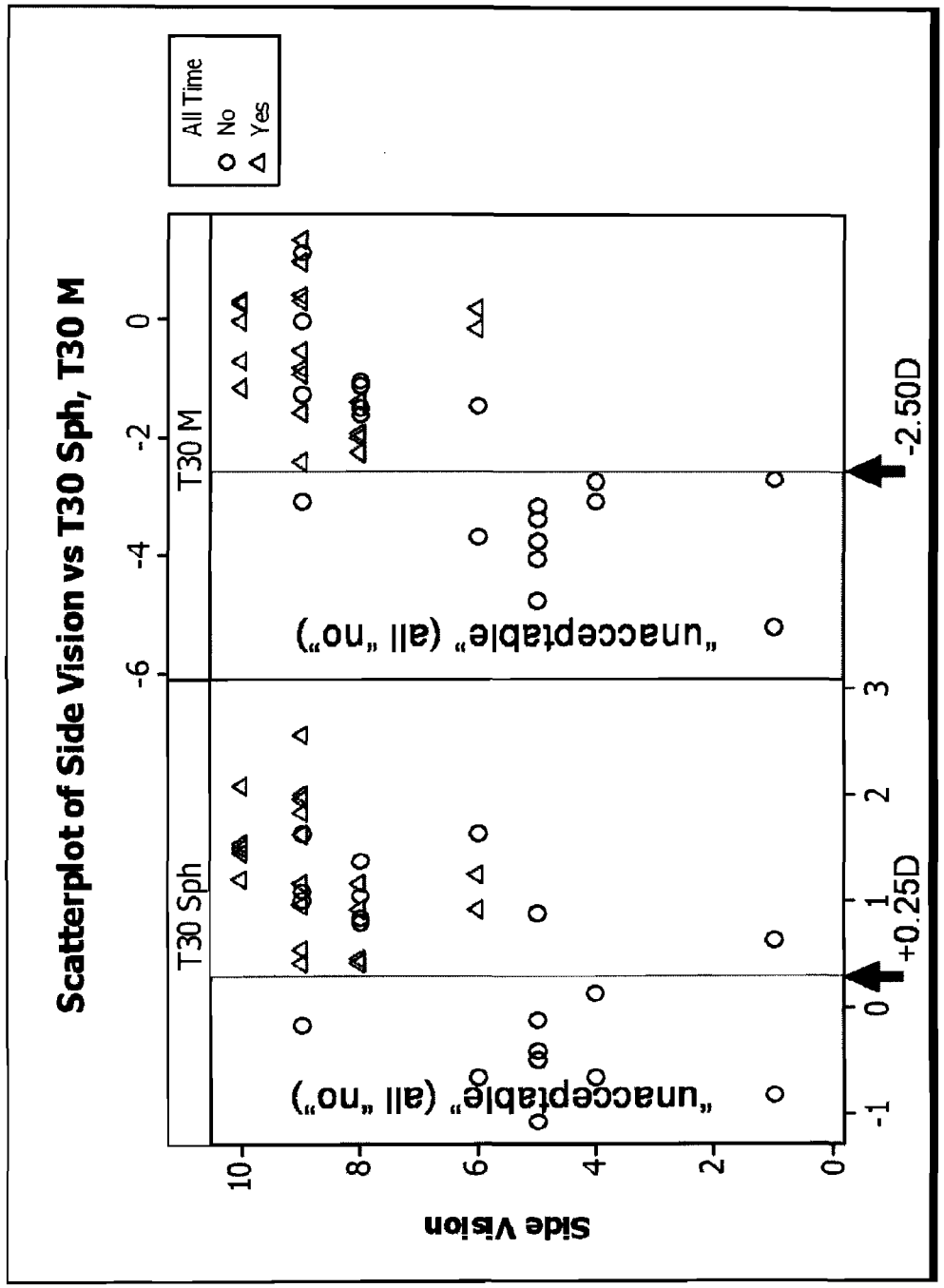
FIG. 24 is a representation of the effect of peripheral refraction in terms of sphere refraction and sphere equivalent on rated side vision quality.

Correlation analysis between subjective vision quality and objective auto-refraction in the retinal periphery of patients who reported differences in vision quality between lenses of various peripheral defocus powers revealed that over-correction limits exist, beyond which vision quality is not acceptable. Turning to FIG. 24, there is shown a representation of the effect of peripheral refraction on the rating of side vision quality for the lenses, using a scale from 0-10. Symbols indicate those patients subjects who answered "no" (circles) or "yes" (triangles) to the question whether vision quality is sufficient to wear the lens all the time.

The plot as shown in FIG. 24 is in terms of sphere refraction ("Sph"; left side of plot) and sphere equivalent refraction ("M"; right side of plot) as measured at 30 degrees in the temporal retina (nasal field) ("T30") by auto-refractometry. If, for example at 30 degrees in the temporal retina (nasal field), the lens produces a sphere refraction below about +0.25 D (i.e. on the retina or in front of the retina), then vision quality is unacceptable as indicated by all patients answering "no" to the question whether vision quality is sufficient to wear the lens all the time. This is shown in the plot in the shaded left side of the "T30 Sph" portion. Similarly, for a sphere equivalent refraction below about −2.50 D (i.e. further in front of the retina than −2.50 D), vision quality is unacceptable as indicated by all patients answering "no" to the question whether vision quality is sufficient to wear the lens all the time (shaded left side of the "T30 M" portion.). Therefore, it can be seen that over-correction of peripheral refraction leads to reduced subjective vision. In particular the sphere meridian should not be corrected to less than +0.25 D and the sphere equivalent meridian to less than −2.50 D. The correlation analysis also indicated that lens rejection is chiefly caused by decreased peripheral vision as opposed to central vision. The identification and application of these over-correction limits substantially facilitates the lens fitting procedure, and helps reduce vision degradation and lens rejection by the patient when correcting peripheral defocus and controlling refractive error development.

Figure 25:
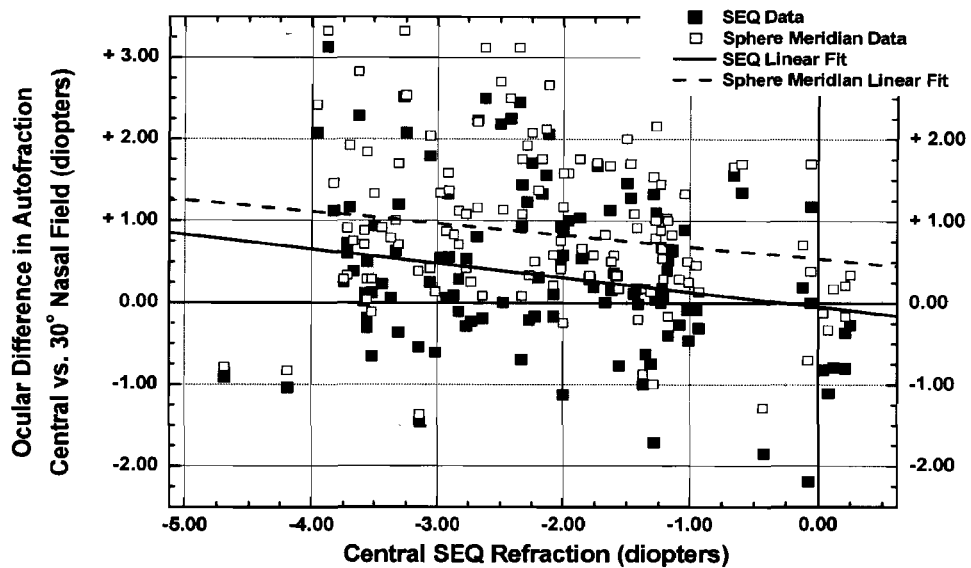
FIG. 25 is a graph plotting central sphere equivalent refraction against the refractive difference between central and 30 degree nasally offset autorefractions, for both sphere meridian and sphere equivalents.

Turning now to FIG. 25, there is shown a scatterplot of both sphere meridian and sphere equivalent (SEQ) data which plots the central sphere equivalent refraction (in diopters) against the refractive difference (also in diopters) between central and 30 degree nasally offset autorefractions. These data were obtained from a largely adult population made up of Caucasian subjects. As can be seen in FIG. 25, for central sphere equivalent (SEQ) refractive errors between +0.50 and −5.00 D, there is a significant increase the peripheral refractive differential with increase in myopia. The rate of increase or slope of a best fit line for these data is 0.14 D/D for sphere meridian and 0.18 D/D for the SEQ. The intercepts (x=0 or plano refractive error) are +0.53 D for sphere meridian and 0.05 D for the SEQ. Therefore, targeting correction or reduction of peripheral refractive differentials for either the sphere meridian or SEQ requires an increase at about the same rate with central SEQ refractions.

Figure 26:
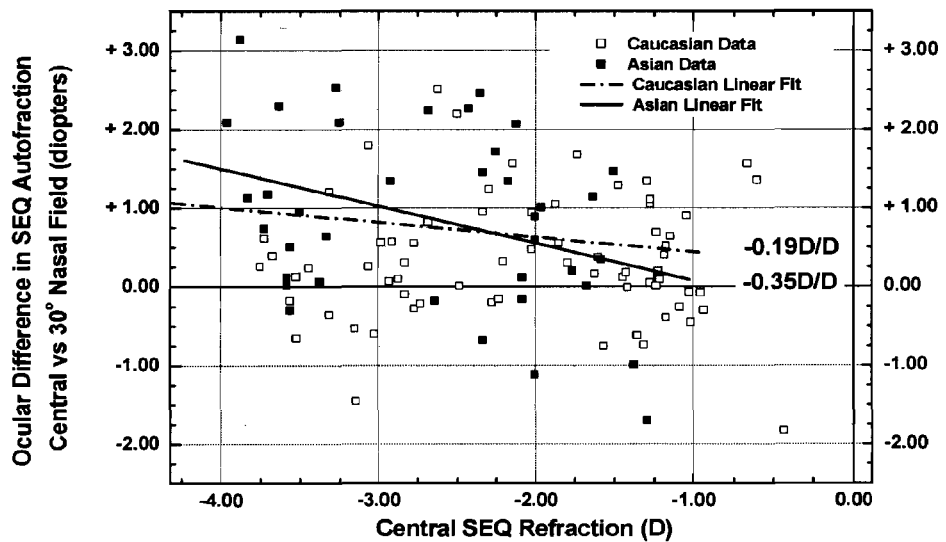
FIG. 26 is a graph plotting central sphere equivalent refraction against the refractive difference (sphere equivalent) between central and 30 degree nasally offset autorefractions, for two test populations.

In FIG. 26, there is shown a scatterplot of the central sphere equivalent (SEQ) refraction data that was shown in FIG. 25, which is also plotted with data of the central sphere equivalent (SEQ) refractions obtained from a population made up of Asian (Chinese) child and adolescent subjects. These data are plotted against the sphere equivalent refractive difference (also in diopters) between central and 30 degree nasally offset autorefractions. Comparison of Caucasian and Asian populations, with SEQ refractive errors between −0.50 and −4.00 D, shows a significant difference in the increase the peripheral refractive differential with increase in myopia. The rate of increase or slope of a best fit line for these data is −0.19 D/D for the Caucasian population measured and −0.35 D/D for the Asian population measured. Therefore, targeting correction or reduction of peripheral refractive differential requires an increase with central SEQ refractions (as noted above with respect to FIG. 25); however, that increase may change depending on the target population's makeup or environmental demographics.

Figure 27:
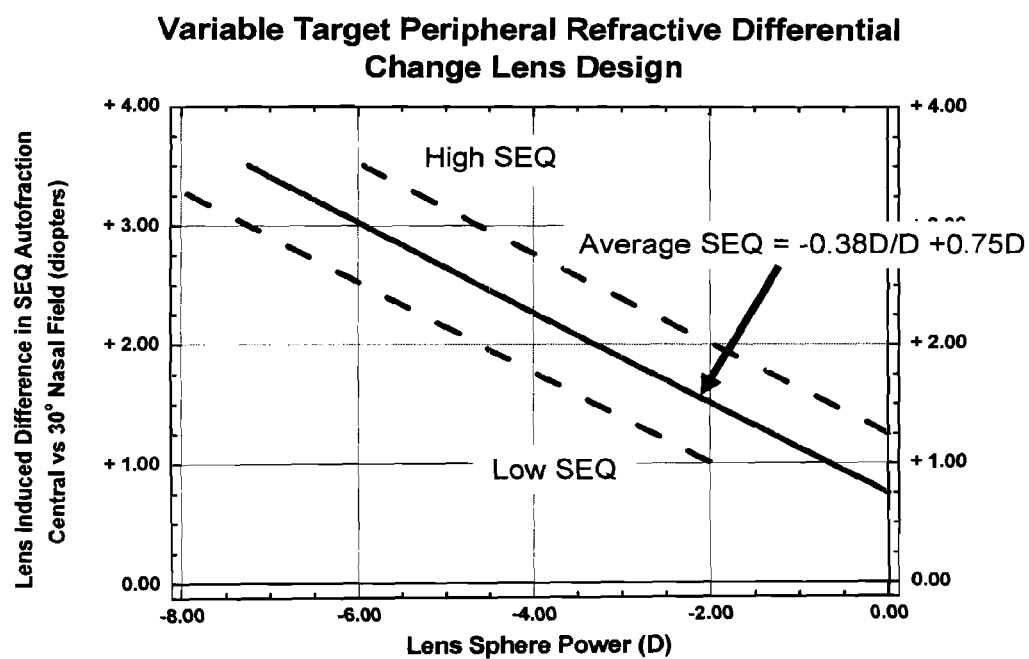
FIG. 27 is a representation of an example lens provision scheme having "Low", "Average" and "High" target correction series.

In certain embodiments, varying the peripheral defocus for each sphere power still may not cover the full range of relative peripheral refractions needed to fit all myopic patients' relative peripheral hyperopic defocus without clinically significant over and under correction in some individuals. In this case, the target correction of the ophthalmic lens can be matched to the change in peripheral refractive differential and an additional variation such as providing an average, a lower than average and a higher than average central to peripheral differential lens power (peripheral defocus) may be needed for each sphere power. While varying the peripheral defocus with central sphere power allows for the change in the average relative peripheral hyperopic defocus, the wide range in the population may need a higher and lower optical design factor to further avoid clinically significant over or under correction of individual patients' relative peripheral refraction. In the example shown in FIG. 27, the target correction or "Average SEQ" correction is to correct the peripheral refractive SEQ differential to +0.75 diopters, and to account for a wide range in the population further higher and lower peripheral refractive SEQ differential targets are shown by the dashed lines designated "High SEQ" and "Low SEQ". In this combination the average central to peripheral differential power will still increase with the minus sphere power to correct for the overall increase in central to peripheral differential refraction with increasing myopia.

In an alternative embodiment, a contact lens may be designed with a negative power differential to provide hyperopic defocus in the central and retinal periphery for the stimulation of axial eye growth in hyperopic eyes. In a further alternative embodiment, a contact lens is designed with a sphero-cylindrical central power for correcting astigmatism. In this case, either the sphere part or the spherical equivalent (sphere+half of the cylinder) of the central power is used as central sphere power for defining the desired peripheral defocus of the lens. A further alternative embodiment of the present invention would include custom prescription of the peripheral defocus based on the patient's individual central to peripheral refraction of the eye. This would be a custom 'made to order' correction and not the more common inventoried approaches as are described above.

It will be appreciated that many modifications of or additions to the sets, kits or stocks of lenses, and to lenses or lens components per se, described in the example, or to their methods of use, can be made by those skilled in the art without departing from the scope of the invention as set out in the following claims.

The invention claimed is:

1. A method of supplying, prescribing or selecting an anti-myopia lens for a myopic eye of a patient, comprising the steps of:
measuring the central refractive error of the myopic eye,
taking the patient's history to assess the patient's propensity for progressive myopia, including the patient's familial history of myopia,
without measuring peripheral refractive error in the eye, assessing the level of propensity of the patient for progressive myopia by having regard to the patent history,
selecting from a set, kit or stock of pre-manufactured lenses a first selected lens having (i) a central corrective refractive power that best matches the measured central refractive error and (ii) a level of peripheral myopic defocus that best matches the assessed propensity for progressive myopia,
trying said first selected lens on the myopic eye and determining from the response of the patient whether or not peripheral blur associated with said myopic defocus of the first selected lens is acceptable,
if the level of myopic defocus is determined to be acceptable, then supplying or prescribing an anti-myopia lens having the central power and the peripheral defocus of the first selected lens for the patient,
if the level of myopic defocus of the first selected lens is determined to be unacceptable, then selecting a further lens from said set, kit or stock of lenses having the same the same central corrective power as the first selected lens but having a reduced level of peripheral myopic defocus, and supplying or prescribing for the patient an anti-myopia lens having the central corrective refractive power and the reduced level of peripheral myopic defocus of said further selected lens.

2. A method according to claim 1 wherein;
said set, kit or stock of lenses is a set, kit or stock of pre-manufactured lenses for use in the provision of an anti-myopia lens for an eye of a myopic patient, wherein:
each lens of the set, kit or stock has a central optical axis and a central optical zone surrounding and including said axis,
said central optical zone has a corrective refractive power between plano and −6.0 D,
each lens has a peripheral optical zone surrounding said central zone,
said peripheral zone includes an incident angle with respect to the optical axis of about 30 degrees,
said peripheral zone of each lens has a positive peripheral refractive power relative to the refractive power of the central zone of that lens to thereby provide myopic peripheral defocus,
said peripheral defocus of any lens within the set, kit or stock of lenses is not greater than about 3.5 D, and
the lenses of the set, kit or stock are arranged in an orderly manner;
whereby a clinician is enabled, by selecting a lens for corrective power to provide or procure a lens to inhibit progression of myopia in the patient's eye and to order a lens with customized peripheral power.

3. A method of supplying, prescribing or selecting for a myopic eye of a patient an anti-myopia lens from a pre-manufactured set, kit or stock of lenses, the set, kit or stock of lenses having multiple lenses with the same central corrective refractive power but with different levels of myopic peripheral defocus, the method comprising the steps of:
measuring the central refractive error of the myopic eye,
taking the patient's history to assess the patient's propensity for progressive myopia, including the patient's familial history of myopia, and without measuring peripheral refractive error in the eye,
supplying, prescribing or selecting a lens from said set, kit or stock having (i) a central refractive power to correct the measured refractive error and (ii) the level of myopic peripheral defocus corresponding to assessed propensity for progressive myopia.

4. A method of supplying, prescribing or selecting an anti-myopia lens for a myopic eye of a patient who wears habitual spectacles, the method comprising the steps of:

measuring the central refractive error of the myopic eye,
taking the patient's history to assess the patient's propensity for progressive myopia, including the patient's familial history of myopia, and without measuring peripheral refractive error in the eye,
supplying, prescribing or selecting a lens from said set, kit or stock having (i) a central refractive power to correct the measured refractive error and (ii) the level of myopic peripheral defocus corresponding to assessed propensity for progressive myopia.

* * * * *